(12) United States Patent
Belhe et al.

(10) Patent No.: US 11,737,900 B2
(45) Date of Patent: Aug. 29, 2023

(54) SYSTEMS AND METHODS FOR ANCHORING AND RESTRAINING GASTROINTESTINAL PROSTHESES

(71) Applicant: MetaModix, Inc., 3650 Annapolis Lane North Suite #1, MN (US)

(72) Inventors: Kedar R. Belhe, Minnetonka, MN (US); Werner Schwarz, Ruhpolding (DE); Todd Stangenes, Mineapolis, MN (US)

(73) Assignee: MetaModix, Inc., Plymouth, MN (US)

( * ) Notice: Subject to any disclaimer, the term of this patent is extended or adjusted under 35 U.S.C. 154(b) by 230 days.

(21) Appl. No.: 16/370,175

(22) Filed: Mar. 29, 2019

(65) Prior Publication Data
US 2019/0298560 A1 Oct. 3, 2019

Related U.S. Application Data

(60) Provisional application No. 62/650,923, filed on Mar. 30, 2018.

(51) Int. Cl.
*A61F 2/04* (2013.01)
*A61F 5/00* (2006.01)

(52) U.S. Cl.
CPC ............. *A61F 5/0079* (2013.01); *A61F 2/04* (2013.01); *A61F 2002/045* (2013.01)

(58) Field of Classification Search
CPC .... A61F 5/0079; A61F 5/04; A61F 2002/045; A61F 2/848; A61F 2002/8483; A61F 2220/0016; A61B 2017/0419
See application file for complete search history.

(56) References Cited

U.S. PATENT DOCUMENTS

| | | | | |
|---|---|---|---|---|
| 5,041,129 | A | * | 8/1991 | Hayhurst ........... A61B 17/0401 606/232 |
| 2004/0107004 | A1 | * | 6/2004 | Levine ..................... A61F 2/04 623/23.64 |
| 2006/0265042 | A1 | * | 11/2006 | Catanese, III ... A61B 17/06109 623/1.11 |
| 2008/0065120 | A1 | * | 3/2008 | Zannis ............... A61B 17/0469 606/144 |
| 2008/0109087 | A1 | | 5/2008 | Durgin |
| 2012/0004676 | A1 | | 1/2012 | Vargas |

(Continued)

OTHER PUBLICATIONS

International Search Report and Written Opinion received for PCT Patent Application No. PCT/US2019/024950, dated Jul. 30, 2019, 11 pages.

(Continued)

*Primary Examiner* — Ariana Zimbouski
(74) *Attorney, Agent, or Firm* — Faegre Drinker Biddle & Reath LLP

(57) ABSTRACT

Systems and methods for anchoring and restraining gastrointestinal prostheses are disclosed. In various examples, the systems and methods include securing a gastrointestinal device within a patient's anatomy by extending an anti-migration anchor through a plurality of portions of the gastrointestinal device to couple together the plurality of portions of the gastrointestinal device. In some examples, the anti-migration anchor extends through tissue situated between the plurality of portions of the gastrointestinal device.

14 Claims, 29 Drawing Sheets

(56) References Cited

U.S. PATENT DOCUMENTS

| | | | |
|---|---|---|---|
| 2012/0184893 A1* | 7/2012 | Thompson | A61F 5/0076 |
| | | | 604/9 |
| 2013/0030351 A1* | 1/2013 | Belhe | A61F 5/0076 |
| | | | 604/9 |
| 2014/0018719 A1 | 1/2014 | Chamorro et al. | |
| 2016/0193023 A1* | 7/2016 | Pereira | A61B 17/06061 |
| | | | 600/37 |
| 2017/0333240 A1 | 11/2017 | Stangenes et al. | |
| 2019/0015091 A1* | 1/2019 | Guo | A61B 17/0469 |

OTHER PUBLICATIONS

The International Search Report and Written Opinion issued in PCT/US19/24950, dated Jul. 30, 2019, 18 pages.

\* cited by examiner

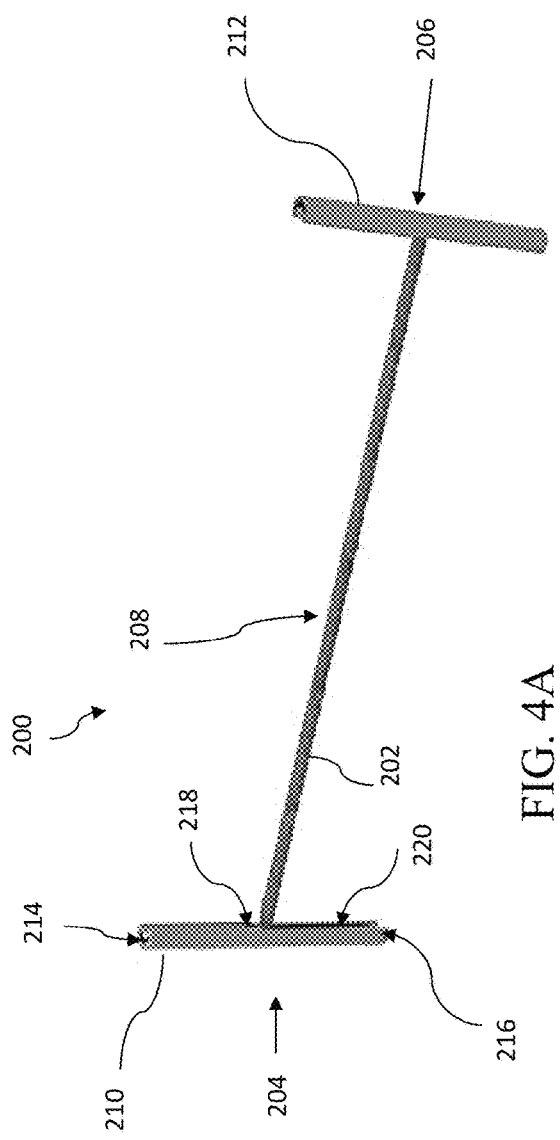
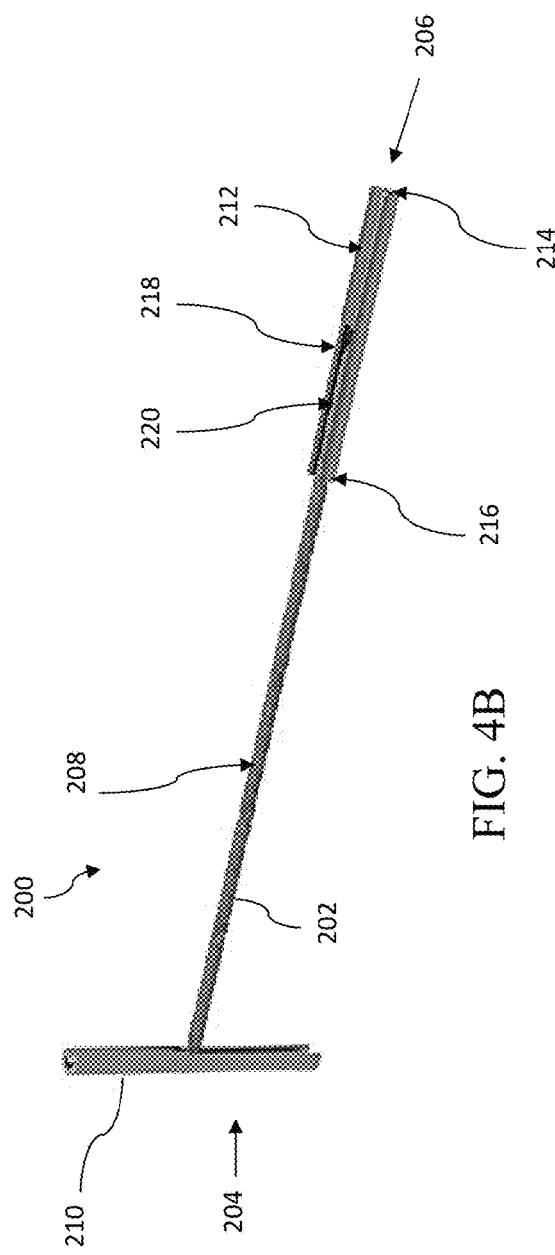

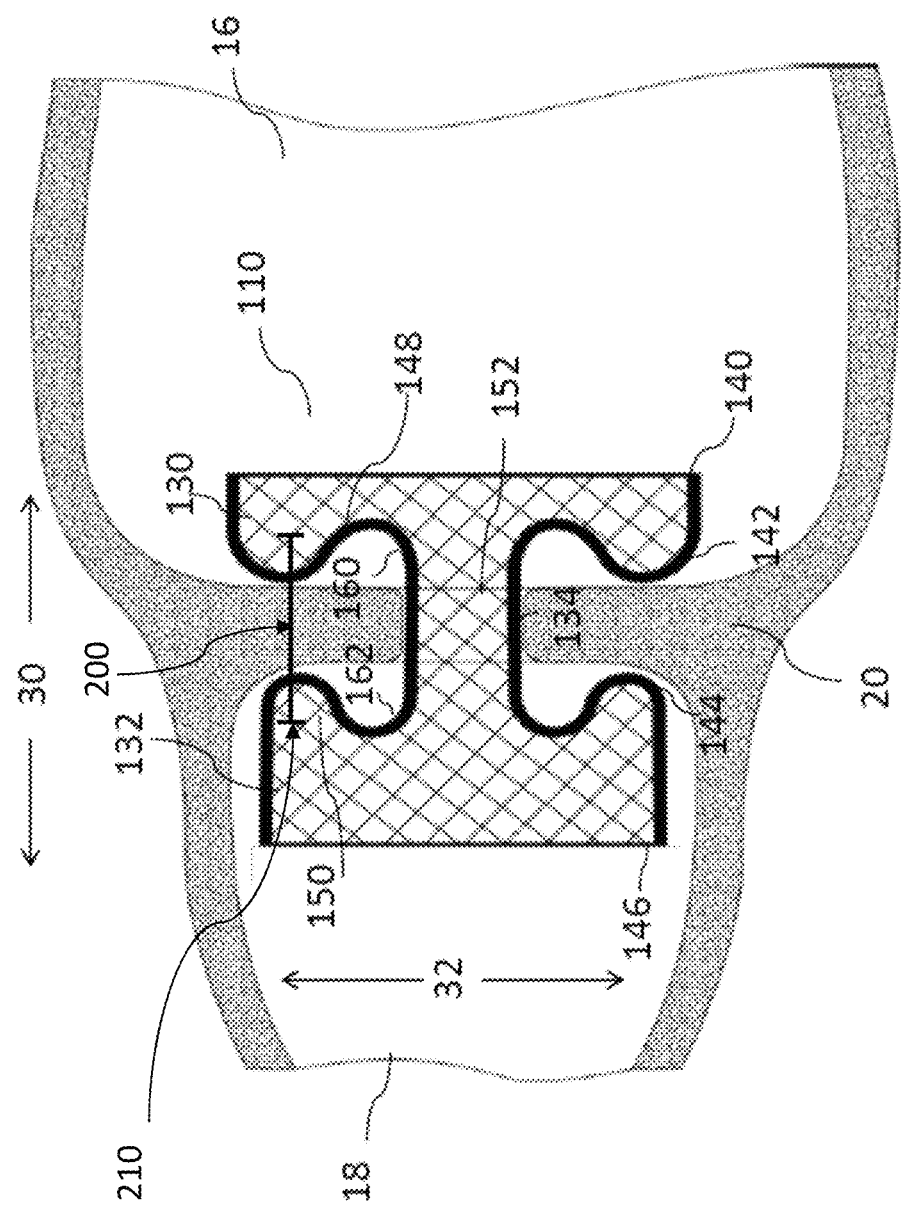

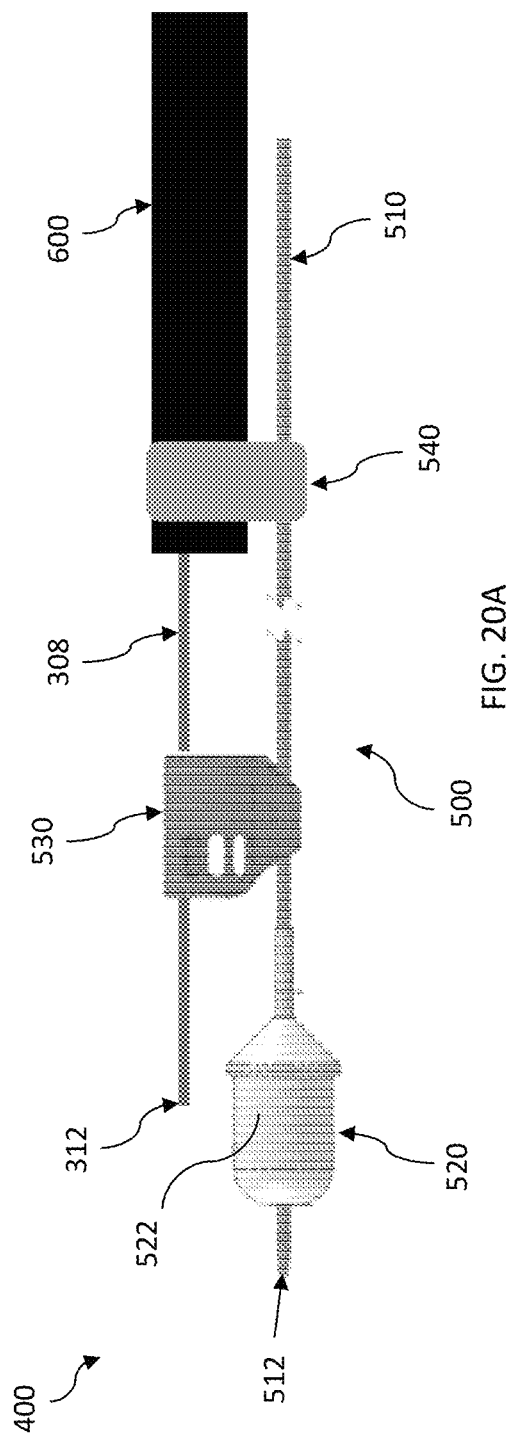
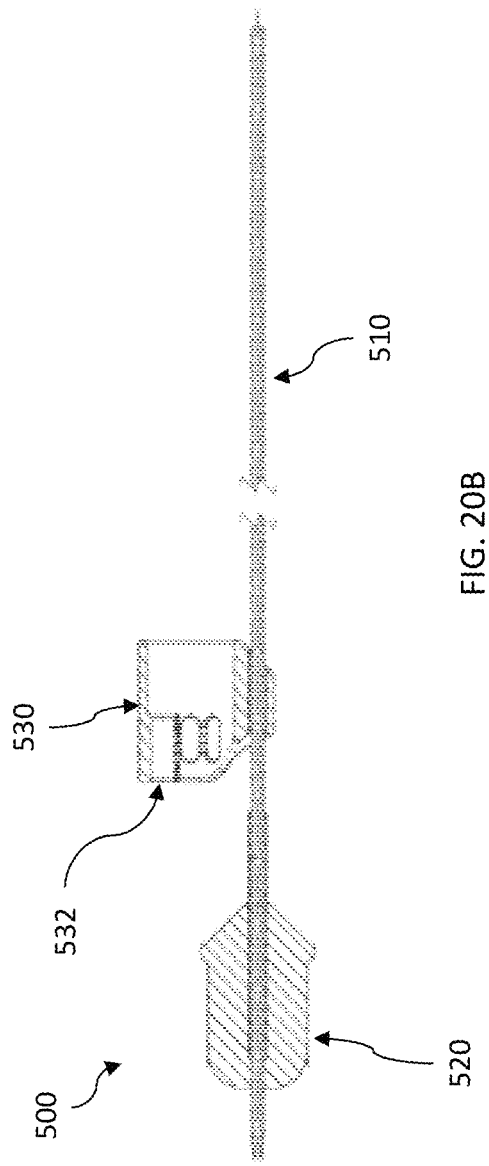

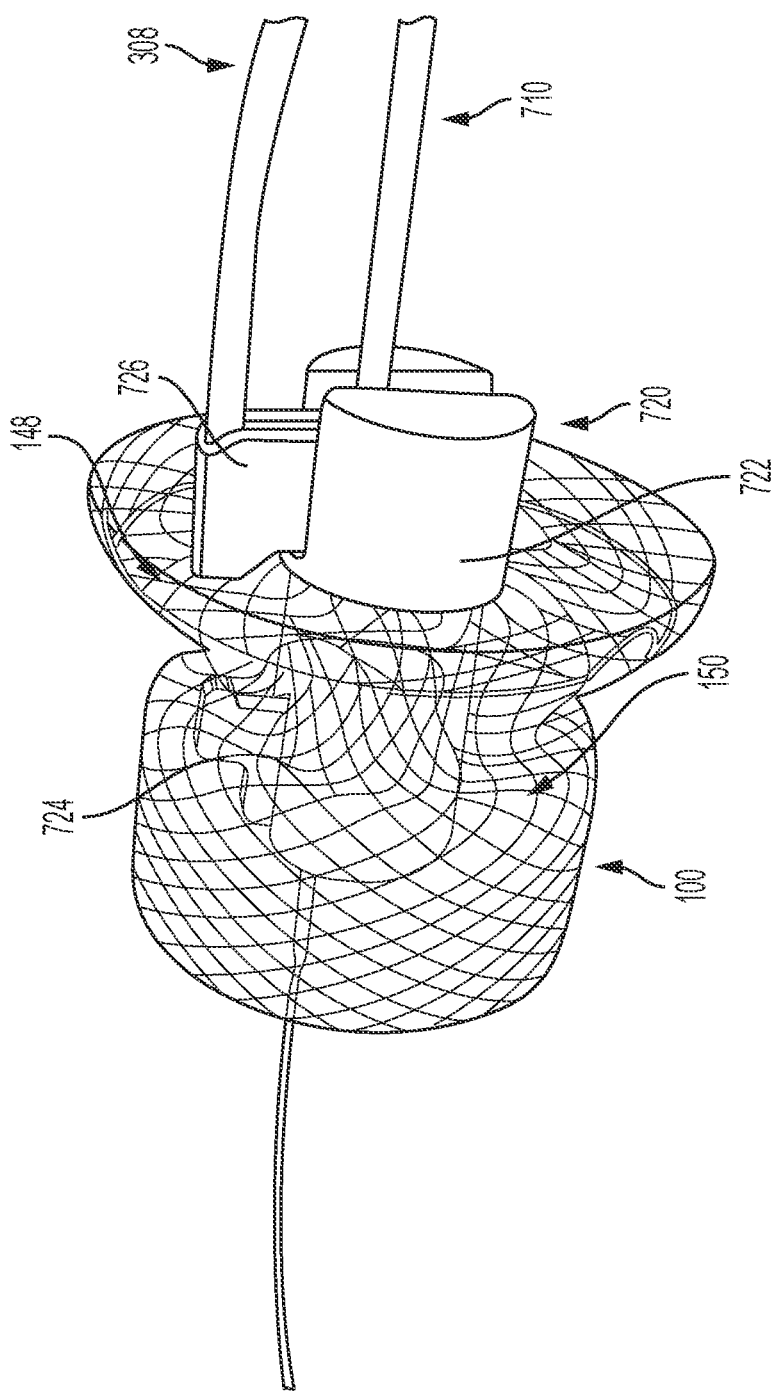

SYSTEMS AND METHODS FOR ANCHORING AND RESTRAINING GASTROINTESTINAL PROSTHESES

CROSS-REFERENCE TO RELATED APPLICATION

The present application claims the benefit of U.S. Provisional Patent Application No. 62/650,923 filed Mar. 30, 2018, which is incorporated herein by reference in its entirety.

TECHNICAL FIELD

The instant disclosure relates generally to implants placed within gastrointestinal tract, including, the stomach and the small intestine. More particularly, it relates to devices and methods for implanting and retrieving systems having components implantable and removable using endoscopic techniques for treatment of obesity, diabetes, Non-Alcoholic Fatty Liver Disease (NAFLD), gastroparesis and other gastrointestinal conditions.

BACKGROUND

Bariatric surgery procedures, such as sleeve gastrectomy, the Roux-en-Y gastric bypass (RYGB) and the bileo-pancreatic diversion (BPD), modify food intake and/or absorption within the gastrointestinal system to effect weight loss in obese patients. These procedures affect metabolic processes within the gastrointestinal system, by either short circuiting certain natural pathways or creating different interactions between the consumed food, the digestive tract, its secretions and the neuro-hormonal system regulating food intake and metabolism. In the last few years, there has been a growing clinical consensus that obese patients who undergo bariatric surgery see a remarkable resolution of their type-2 Diabetes Mellitus (T2DM) soon after the procedure. The remarkable resolution of diabetes after RYGB and BPD typically occurs too fast to be accounted for by weight loss alone, suggesting there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery with potentially serious complications and long patient recovery periods. In recent years, there has been increased effort to develop minimally invasive procedures to mimic the effects of bariatric surgery. Many such procedures involve the use of gastrointestinal implants within the stomach or the small intestine that modify transport and absorption of food and organ secretions. One of the principal challenges with such procedures includes the difficulty in safely anchoring implants in the dynamic environment of the gastrointestinal tract, due to the intermittent and complex peristaltic motion within the gastrointestinal tract. Attempts have been made to secure implants within the gastrointestinal tract with means such as sutures, staples and barbs. For example, U.S. Pat. No. 7,476,256 describes an implant having a tubular sleeve with anchoring barbs, which penetrate the wall of the small intestine. However, stents with active fixation means, such as the barbs described in U.S. Pat. No. 7,476,256 that penetrate the wall of the stomach or the small intestine into surrounding tissue, may potentially cause tissue necrosis and erosion of the implants through the tissue. These systems are also associated with risks that penetrating the walls of the stomach or the small intestine establish a pathway for bacterial translocation from the non-sterile environment inside the gastro-intestinal tract into the sterile environment of the various organs in the abdominal cavity. This increases the risk of infections of the surrounding organs such as the liver and the pancreas and can pose a very serious health risk and require aggressive treatment including surgery.

SUMMARY

According to one example ("Example 1") a gastrointestinal implant system includes an implant configured to be implanted within a pylorus of a patient, the implant having a proximal portion, a distal portion, and a neck portion situated between the proximal and distal portions, the neck portion being configured to span a pyloric sphincter of the pylorus when implanted, an anti-migration anchor including an elongate element, a first retention feature coupled to the elongate element, and a second retention feature coupled to the elongate element, the anti-migration anchor configured such that the elongate element is operable to span the neck portion of the implant such that the first retention feature is positionable proximal to the proximal portion of the implant and such that second retention feature is positionable distal to the distal portion of the implant.

According to another example ("Example 2") further to Example 1, the first and second retention features are configured to transition between delivery and deployed configurations.

According to another example, ("Example 3") further to Example 2, in the delivery configuration, the first and second retention features extend along the elongate element, and wherein in the deployed configuration, the first and second retention features extend transverse to the elongate element.

According to another example, ("Example 4") further to any of Examples 2 or 3, the first retention feature includes a first end, a second end, and a middle portion situated between the first and second ends, and wherein the elongate element is coupled to the middle portion.

According to another example, ("Example 5") further to any of Examples 2 to 4, one or more of the first and second retention features are biased to transition to the delivery configuration when not constrained.

According to another example, ("Example 6") further to any of the preceding Examples, the anti-migration anchor is configured to extend through a tissue situated between the proximal and distal portions of the implant, thereby securing the implant to the tissue.

According to another example, ("Example 7") further to Example 6, the proximal and distal portions and the neck of the implant form a primary anchor for anchoring the implant to the tissue, and wherein the anti-migration anchor forms a secondary anchor for anchoring the implant to the tissue.

According to another example, ("Example 8") further to any of the preceding Examples, the anti-migration anchor operates to help maintain a geometry of the implant.

According to another example, ("Example 9") further to Example 8, wherein the anti-migration anchor operates to minimize an amount of relative angulation between the proximal and distal portions of the implant by constraining a length between the proximal and distal portions of the implant.

According to another example, ("Example 10") further to any of Examples 8 or 9, the anti-migration anchor constrains an amount of deformation of one or more of the proximal and distal portions of the implant.

According to another example, ("Example 11") further to any of the preceding Examples, the first and second retention features of the anti-migration anchor are configured such that they can only contact the proximal and distal portions of the implant and cannot come in direct contact with the pyloric tissue.

According to another example, ("Example 12") further to any of the preceding Examples, the anti-migration anchor operates to tether the implant to the pylorus when implanted.

According to another example, ("Example 13") further to any of the preceding Examples, the anti-migration anchor operates to firmly affix the implant to the pylorus when implanted.

According to another example, ("Example 14") further to any of the preceding Examples, the anti-migration anchor is implantable after the implant is implanted.

According to another example, ("Example 15") further to any of the preceding Examples, the anti-migration anchor is removable from the implant.

According to another example, ("Example 16") an anti-migration apparatus for retaining a gastrointestinal implant implanted at a pylorus of a patient includes an elongate element, a plurality of retaining tabs including a first retention feature coupled to the elongate element and a second retention feature coupled to the elongate element, the first retention feature operable to transition between a delivery configuration and a deployed configuration, the elongate element configured to span between a proximal portion and a distal portion of the gastrointestinal device such that the first retention feature is positionable proximal to the proximal portion of the gastrointestinal device and such that the second retention feature is positionable distal to the distal portion of the gastrointestinal device.

According to another example, ("Example 17") a method of securing a gastrointestinal implant within a pylorus of a patient includes providing an implant having a proximal portion, a distal portion, and a neck portion situated between the proximal and distal portions, deploying the implant within the pylorus such that neck portion spans the pylorus with the proximal portion of the implant is situated proximal to the pylorus and the distal portion situated distal to the pylorus, providing an anti-migration anchor including an elongate element, a first retention feature coupled to the elongate element, and a second retention feature coupled to the elongate element, after deploying the implant, deploying the anti-migration anchor such that the anti-migration anchor spans the neck portion of the implant and punctures the proximal and distal portions of the implant, and such that the first retention feature is situated proximal to the proximal portion of the implant and such that second retention feature is situated distal to the distal portion of the implant.

According to another example, ("Example 18") further to Example 17, the method further includes deploying the implant within the pylorus such that a tissue of the pylorus is situated proximate the neck portion and between the proximal and distal portions of the implant.

According to another example, ("Example 19") further to any of Examples 17 to 18, the method further includes deploying the anti-migration anchor such that the anti-migration anchor punctures the tissue of the pylorus but does not penetrate the wall of the stomach or the small intestine in to the surrounding abdominal cavity.

According to another example, ("Example 20") further to any of Examples 17 to 19, the method further includes deploying a plurality of anti-migration anchors.

According to another example, ("Example 21") further to any of Examples 17 to 20, the method further includes deploying the plurality of anti-migration anchors such that each anti-migration anchor punctures the tissue.

According to another example, ("Example 22") an anti-migration anchor delivery system transitionable between a delivery configuration and a deployed configuration includes a first catheter, a locator system coupled to the first catheter, the locator system including a locator capsule and a first extendable arm configured to extend radially outwardly from the locator capsule such that in the delivery configuration the first extendable arm is stowed within the locator capsule, and such that in the deployed configuration the first extendable arm projects radially outwardly from the locator capsule, a second catheter coupled to the first extendable arm, the second catheter configured to deliver an anti-migration anchor to an implant deployed within an anatomy of a patient, wherein in the delivery configuration the second catheter is situated in a first radial position relative to the locator capsule and wherein in the deployed configuration the second catheter is situated in a second radial position relative to the locator capsule.

According to another example, ("Example 23") further to Example 22, the locator capsule is situated at a distal end of the first catheter.

According to another example, ("Example 24") further to any of Examples 22 to 23, the second radial position is a radial position that is more radial distant from a longitudinal axis of the locator capsule than is the first radial position.

According to another example, ("Example 25") further to any of Examples 22 to 24, the locator system further comprises a second extendable arm distal to the first extendable arm, the second extendable arm being configured to extend radially outwardly from the locator capsule such that in the delivery configuration the second extendable arm is stowed within the locator capsule, and such that in the deployed configuration the second extendable arm projects radially outwardly from the locator capsule.

According to another example, ("Example 26") further to Example 25, in the delivery configuration the first and second extendable arms are situated at a first longitudinal distance from one another, and such that in the deployed configuration the first and second extendable arms are situated at a second longitudinal distance from one another.

According to another example, ("Example 27") further to Example 26, the second longitudinal distance is shorter than the first longitudinal distance.

According to another example, ("Example 28") an anti-migration anchor delivery system includes a first catheter, a locator system coupled to a distal end of the first catheter, the locator system including a locator capsule and a hood that extends radially outwardly from the first catheter locator capsule, the hood being positioned proximal to the locator capsule, an second catheter configured to deliver an anti-migration anchor to an implant deployed within an anatomy of a patient, wherein the second catheter is configured to be advanced through an endoscope and the hood of the locator system such that the hood constrains the second catheter to designated radial position relative to a longitudinal axis of the locator capsule.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 4A is a front perspective view of a suture tether, according to some embodiments;

FIG. 4B is a front perspective view of a suture tether, according to some embodiments;

FIG. 5 is a cross-sectional view of a portion of the digestive tract in a human body with a gastrointestinal device and a suture tether implanted in the pylorus, according to some embodiments;

FIG. 20A illustrates a gastrointestinal implant delivery system, according to some embodiments FIG. 20B is a cross sectional view of the gastrointestinal implant delivery system taken along a longitudinal axis thereof, according to some embodiments FIGS. 23A-23B illustrate a gastrointestinal implant delivery system in combination with a gastrointestinal device, according to some embodiments

DETAILED DESCRIPTION

Figure 1:
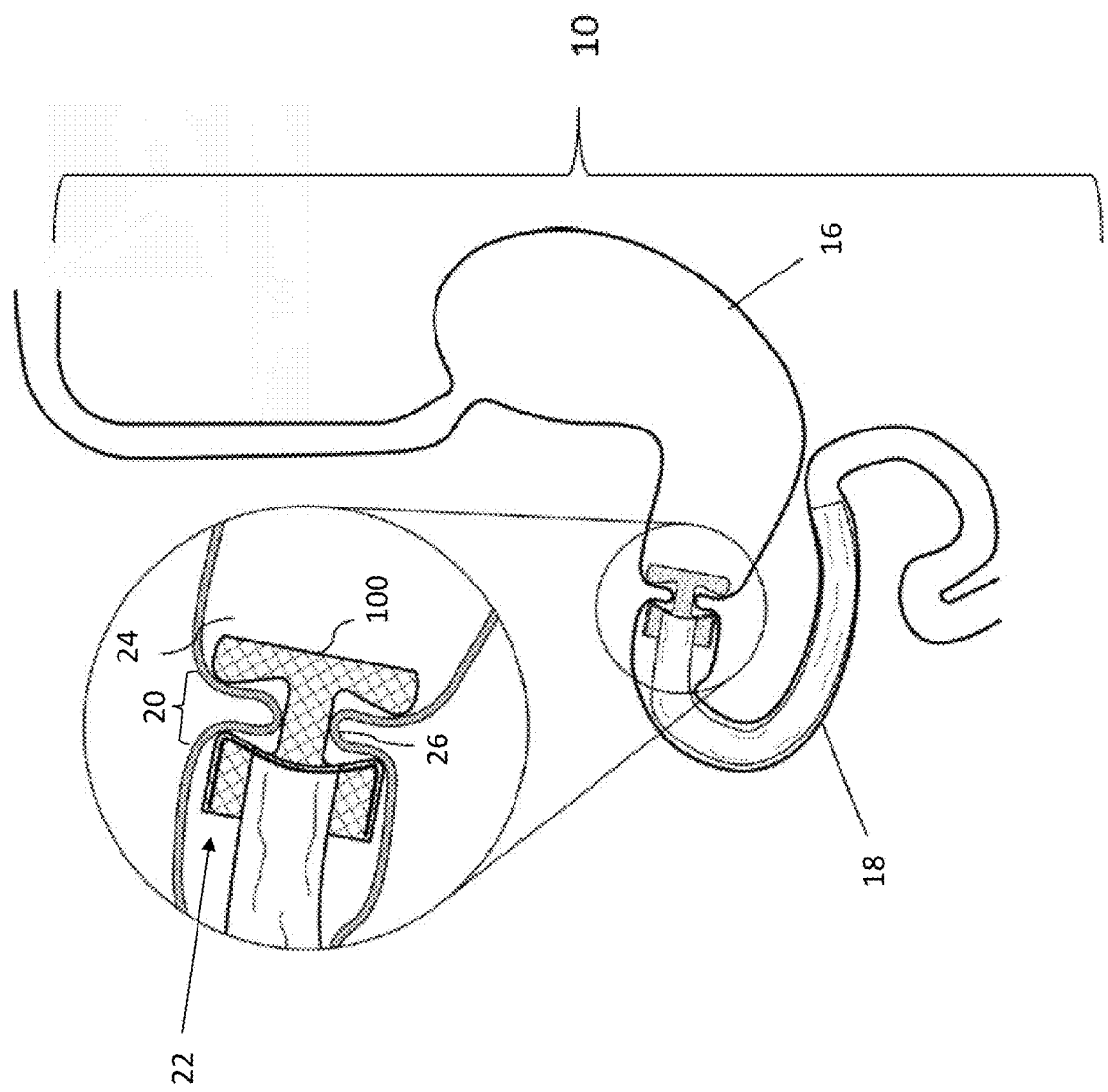
FIG. 1 is a cross-sectional view of a portion of the digestive tract in a human body with a gastrointestinal device positioned in the pylorus, according to some embodiments.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present disclosure relates to apparatuses, systems, and methods to place and remove apparatuses and systems within an anatomy of a patient. Using the apparatuses, systems, and methods disclosed herein, an implantable device may be placed (e.g., delivered and/or deployed) and/or retrieved from within the patient's anatomy. In various embodiments, such procedures are conducted endoscopically through the mouth, throat, stomach and intestine. Some examples relate to apparatuses, systems, and methods for placing and/or retrieving an implantable medical device from within the gastrointestinal tract of a patient, such as within the pyloric antrum, pylorus, duodenum and/or the jejunum of a patient. It will be appreciated that, in various examples, such medical devices may be delivered via one or more catheters.

In some instances, the apparatuses, systems, and methods disclosed herein may be used to secure a position of a medical device, such as a gastrointestinal device, within the patient's anatomy. For instance, in some examples, one or more anchoring elements may be utilized to secure a gastrointestinal device within a particular portion of the patient's stomach, and/or intestine, including the pyloric antrum, pylorus, duodenum, and/or jejunum. In various embodiments, these apparatuses and systems may be removed. For instance, the anchoring element(s) and gastrointestinal device may be removed after a designated period of time, or in response to an occurrence of one or more events.

As discussed in greater detail below, in various embodiments, an anchoring means, such as one or more anchoring elements, operates to tether a gastrointestinal implant to the pylorus at the base of the stomach. The pylorus is a muscular body that works as a sphincter by opening and closing with relaxation and contraction of circular muscles, thereby including a circular aperture at the base of the stomach, which acts as a valve. When fully open, the pylorus generally exhibits a maximum diameter of between twelve millimeters (12 mm) and thirty millimeters (30 mm).

Thus, the disclosed systems, devices, and methods do not penetrate from within the digestive tract into the abdominal cavity, thereby minimizing risks of bacterial translocation and subsequent infection. In various examples, the delivery system is operable to deliver a suture tether through the muscular portion of the pylorus which is contained within the non-sterile environment of the gastrointestinal tract. In some examples, the delivery system additionally includes one or more features and/or attributes that operate to minimize a risk of penetrating the sterile environment of the surrounding abdominal cavity. In some examples, the delivery system additionally includes one or more features that operate to minimize or otherwise protect the pylorus from excessive forces that could cause tears, pressure necrosis or ulceration.

FIG. 1 shows a cross-sectional view of a portion of a human digestive tract 10, showing a stomach 16, intestine 18, the pylorus 20, and the duodenum 22. The pylorus generally includes the pyloric antrum 24 and the pyloric sphincter 26. As shown in FIG. 1, a gastrointestinal device 100 may be positioned between the stomach 16 and the intestine 18. In some examples, the gastrointestinal device 100 is positioned within the pylorus 20 such that one or more portions of the gastrointestinal device 100 are positioned within or adjacent to the pyloric antrum 24. In some examples, the gastrointestinal device 100 is additionally or alternatively positioned with one or more portions of the gastrointestinal device 100 positioned within the duodenum 22.

Figure 2:
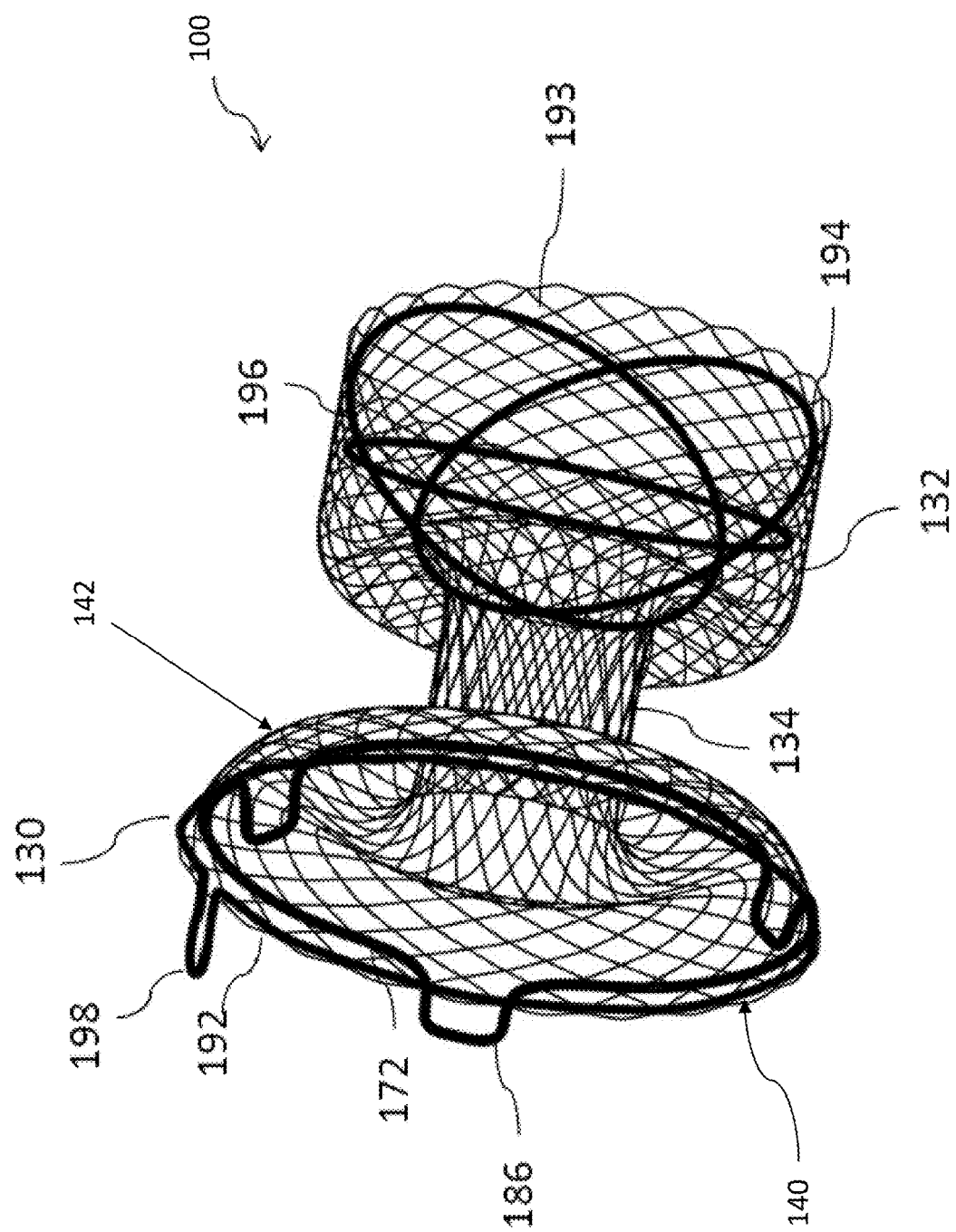
FIG. 2 is a schematic view of a gastrointestinal device, according to some embodiments.
Figure 3:
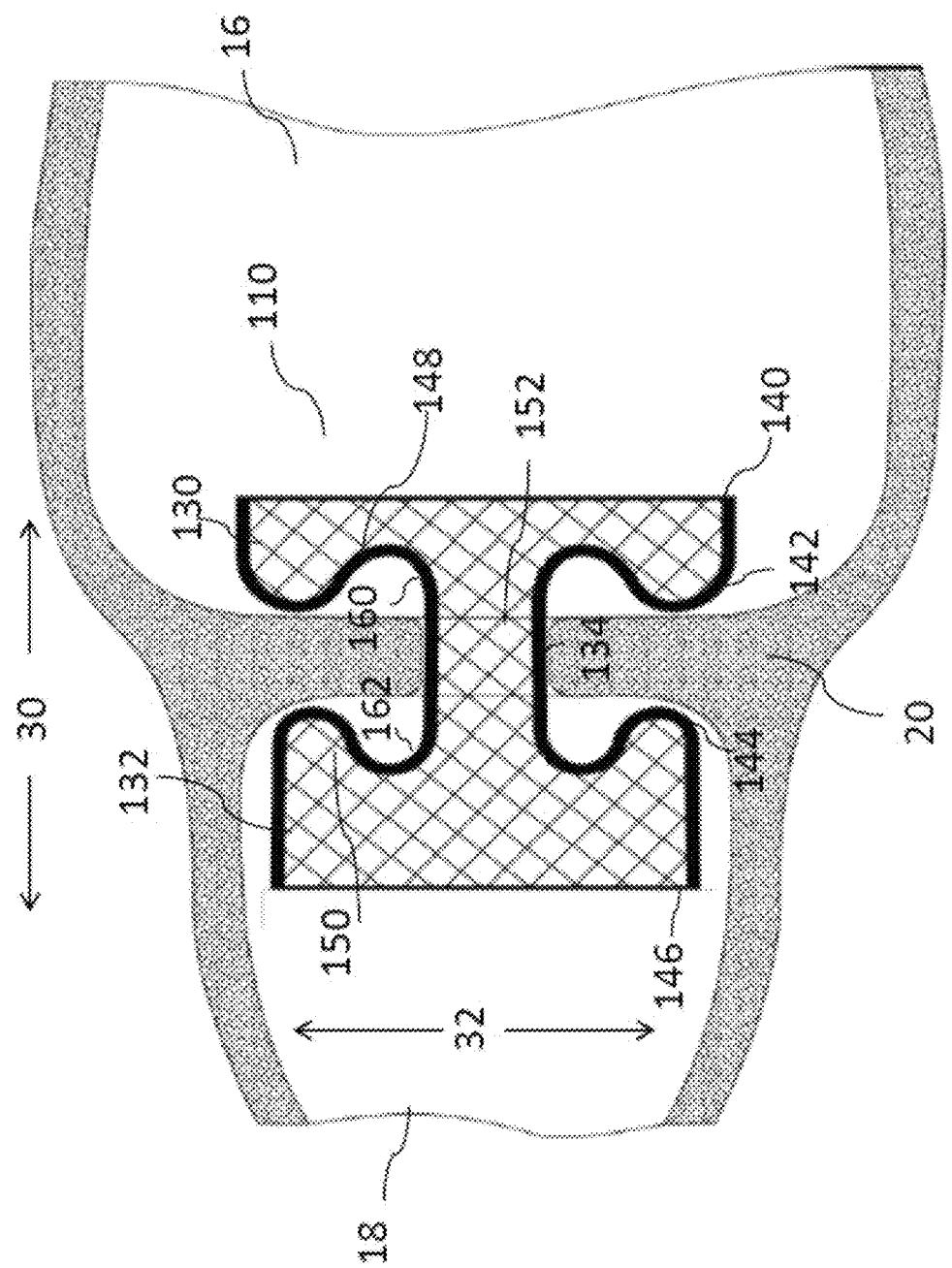
FIG. 3 is a cross-sectional view of a portion of the digestive tract in a human body with a gastrointestinal device implanted in the pylorus, according to some embodiments.

FIGS. 2 and 3 show a gastrointestinal device 100 according to various embodiments. FIG. 2 is a perspective view of the gastrointestinal device 100. FIG. 3 is a cross section view of a simplified form of the gastrointestinal device 100 in a patient's anatomy, illustrated with the proximal and distal structural elements 172 and 196 removed for clarity.

In various embodiments, the gastrointestinal device 100 is an expandable, endoscopically deliverable component that interfaces with native anatomy within the gastrointestinal tract to help effectuate weight loss. In some examples, the gastrointestinal device 100 is expandable, as those of skill will appreciate. That is, in various embodiments, upon deployment, the gastrointestinal device 100 can transition from a compressed or collapsed delivery configuration to an expanded deployed configuration. Although not shown in FIG. 2 or 3, it will be appreciated that, in various examples, a sleeve may be attached or may be attachable to the gastrointestinal device 100, upon deployment, the sleeve 120 may be positioned or positionable within the intestine 18 of the patient, as those of skill will appreciate. Thus, in various examples, the bypass sleeve may be an intestinal bypass sleeve, an intestinal liner, or a bypass liner.

With continued reference to FIGS. 2 and 3, the gastrointestinal device 100 has a generally cylindrical shape. In some embodiments, the gastrointestinal device 100 defines a central longitudinal axis along a length of the gastrointestinal device 100. The gastrointestinal device 100 also generally includes a proximal portion 130, a distal portion 132, and a neck portion 134. In various examples, the neck portion 134 is situated between the proximal portion 130 and the distal portion 132. The neck portion 134 may be integral with the proximal and distal portions 130 and 132, or may alternatively be coupled to the proximal and distal portions 130 and 132. In various examples, the neck portion 134 fluidly couples the proximal and distal portions 130 and 132. In some examples, the neck portion 134 is tubular and includes a lumen therethrough. In some such examples, the lumen extends along the longitudinal axis of the gastrointestinal device 100.

In some examples, the proximal portion 130 includes a proximal end 140, and a distal end 142. In some examples, the proximal portion 130 is cylindrical or tubular shaped. In some embodiments, a proximal wall flange 148 is situated between the proximal portion 130 and the neck portion 134. In some examples, a diameter of an outer surface of the proximal portion 130 is larger than a diameter of an outer surface of the neck portion 134. Thus, in various examples, the proximal wall flange 148 is generally disk-shaped and extends between the neck portion 134 and the proximal portion 130, as shown. In some examples, the proximal wall flange 148 is oriented transverse to the central longitudinal axis of the gastrointestinal device 100.

In various embodiments, one or more of the proximal portion 130 and the proximal wall flange 148 adopt a curved profile or are otherwise predisposed to have a curved profile when deployed (e.g., when the gastrointestinal device 100 is expanded). For instance, in some examples, one or more of the proximal portion 130 and the proximal wall flange 148 include a concavity. For example, the proximal wall flange 148 may resemble a bowl. In some other examples, one or more of the proximal portion 130 and the proximal wall flange 148 additionally or alternatively include a convexity.

In some embodiments, the distal portion 132 includes a proximal end 144, a distal end 146 and an outer wall extending in between proximal and distal ends 144 and 146. In some examples, the distal portion 132 is shaped as a flange. In some examples, the distal portion 132 is cylindrical. In some examples, a distal wall flange 150 is situated between the distal portion 132 and the neck portion 134. In some examples, a diameter of an outer surface of the distal portion 132 is larger than the diameter of the outer surface of the neck portion 134. Thus, in various examples, the distal wall flange 150 is generally disk-shaped and extends between the neck portion 134 and the distal portion 132, as shown. The distal wall flange 150 generally extends from the proximal end 144 of the distal portion 132. In some examples, the distal wall flange 150 extends transverse to the central longitudinal axis of the gastrointestinal device 100. As discussed in greater detail below, when positioned within a patient, in an expanded configuration, the distal portion 132 may be located in the duodenum, and/or may define an opening at the distal end 146 that faces the intestine 18.

The neck portion 134 comprises a first end 160, a second end 162 and a wall extending between the first and second ends 160, 162. The neck portion 134 may be shaped as a cylinder that extends between the proximal portion 130 and the distal portion 132, as mentioned above. In some examples, the neck portion 134 defines a through-lumen 152 that allows contents of the stomach 16 (e.g., chime) to pass into the intestine 18. The neck portion 134 may be rigid to hold the pylorus 20 open or it may be compliant to allow the opening and closure of the through-lumen 152 with the pylorus 20.

In some embodiments, the length of the neck portion 134 may be approximately the width of a patient's pylorus. In some embodiments, the length of the neck portion 134 may be longer than the width of a patient's pylorus to provide a gap between the proximal wall flange 148, the distal wall flange 150 and the pylorus 20. In some embodiments, the neck portion 134 may be sized to allow the proximal wall flange 148 and the distal wall flange 150 to contact the pylorus 20.

In various embodiments, the gastrointestinal device 100 may be formed from a braided wire structure, as those of skill will appreciate. Such braided wire structure may help position the gastrointestinal device 100 within a patient. For example, the braided wire structure may provide structural support to the gastrointestinal device 100 and help maintain the shape of the gastrointestinal device 100.

In some embodiments, the gastrointestinal device 100 includes a structural element contained within the braided wire structure. As shown in FIG. 2, in some embodiments, the gastrointestinal device 100 has a distal structural element 196. In some examples, the distal structural element 196 is comprised of rings 193, 194 attached to the distal portion 132 and/or the neck portion 134. In some examples, the distal structural element 196 includes a metal such as Nitinol (nickel-titanium alloy), a nickel-cobalt base alloy such as that sold under the tradename MP35N®, a cobalt alloy such as Alloy L605, a cobalt-chromium-nickel-molybdenum alloy such as that sold under the tradename Elgiloy®, stainless steel, or from a plastic such as PET, PEEK, a polyoxymethylene such as that sold under the tradename Delrin® or any other suitable material. In some examples, the distal structural element 196 includes a superelastic Nitinol wire formed into a suitable shape. In an exemplary embodiment, a distal structural element 196 is formed from three rings of Nitinol wire. If the distal structural element 196 is desired with a certain rigidity or stiffness, the size and material that the distal structural element 196 is made from can be used to control these properties. For example, Nitinol wire can be used to form stiffening elements with a suitable compressive and expansive strength as a function of the diameter of the wire used to make the distal structural element 196.

As shown in FIG. 2, the rings 193, 194 of the distal structural element 196 are arranged around the distal portion 132 and are attached to the distal portion 132, such as by being integrally woven into the flange material. The rings 193, 194 of the distal structural element 196 are attached by weaving the rings 193, 194 though the braided structure of the distal portion 132. In some examples the wire ends can be inserted into a connection sleeve and crimped, welded, and/or fastened by any other suitable known means.

As shown in FIG. 2, in some embodiments, the gastrointestinal device 100 additionally or alternatively includes a proximal structural element 172 attached to the proximal portion 130. In some examples, the proximal structural element 172 is a compression biasing element, such as a spring. The proximal structural element 172 may be constructed as a substantially circular frame having nodes 186. The proximal structural element 172 may be constructed from the same material that forms the distal structural element 196. The proximal structural element 172 may also provide structural support to the proximal portion 130. For example, the proximal structural element 172 generally has an overall frame that is compressible, yet also is rigid. The proximal structural element 172 may impart additional radial strength to the proximal portion 130 and help keep the proximal end 140 of the proximal portion 130 open. The proximal structural element 172 can be shaped to bias the direction of collapse of the gastrointestinal device 100 for removal from a patient and for loading the device onto a delivery catheter for delivery within a patient.

As shown in FIG. 2, in some embodiments, the gastrointestinal device 100 may include a drawstring 192. In some examples, the drawstring 192 is attached to the proximal portion 130. The drawstring 192 can be attached to the proximal portion 130 by weaving the drawstring 192 through the material of the proximal portion 130. In various examples, the drawstring may be weaved through the material of the proximal portion and have a portion of the drawstring forming a loop 198. For example, the drawstring 192 may be constructed from a string or suture that is weaved through alternating cells in the braided wire structure of the gastrointestinal device 100. The loop 198 allows the drawstring 192 to be attached to a retraction tool, for example, to a hook or a clamp. In some embodiments, the drawstring 192 is a suture that is weaved through the proximal portion 130. The drawstring 192 may be a separate structure from the proximal structural element 172. The drawstring 192 may be constructed from a suture material and may comprise a thin wire or cable.

Turning back now to FIG. 3, when deployed within the patient's anatomy, the proximal portion 130 is generally located on the side of the pylorus 20 that is adjacent the stomach 16, with the distal portion 132 generally located on the side of the pylorus 20 that is adjacent the duodenum 22, and with the neck portion 134 spanning the pyloric sphincter 26.

As shown the gastrointestinal device 100 is deployed such that the pyloric sphincter 26 and associated tissue is sandwiched between or otherwise situated between the proximal and distal portions 130 and 132 of the gastrointestinal device 100. Conventional designs have traditionally relied on the integrity and geometry of the implanted device to resist migration and or rotation of the implanted device relative to the pylorus 20 and surrounding tissue.

For instance, some conventional devices have sought to resist or minimize rotation and migration after implantation by increasing a length and/or diameter of the portion of the device projecting into the duodenum. Such configurations provide that the device may contact the duodenum and prevent further rotation before becoming deflected or dislodged. For instance, the length and diameter of the portion of the device extending into the duodenum can be sized to prevent canting or tilting within the duodenum. In some embodiments, such configurations provide that upon rotation or canting of the device away relative to the surrounding anatomy, the device will make contact with the intestinal wall and therefore will resist migration further rotation or canting. Some other conventional designs have included active fixation means, such as barbs that deeply penetrate into surrounding tissue. However, as mentioned above, such configurations bear a risk for tissue necrosis and erosion, which can lead to complications, such as bacterial infection of the mucosal tissue or systemic infection.

In some cases, devices have included additional structural components to assist in anchoring the device to the surrounding anatomy, like those structural elements discussed above (e.g., proximal and distal structural elements 172 and 196). These structural elements, however, do not penetrate the surrounding tissue, and thus rely on the geometry of the device and its interference with the surrounding tissue to maintain alignment of the device within the anatomy.

In various embodiments, one or more suture tethers can be utilized in combination with the gastrointestinal device 100 to secure the gastrointestinal device 100 to the surrounding tissue. As explained in greater detail below, the one or more suture tethers operate to secure the gastrointestinal device to the surrounding anatomy, and, in some instances, operate to help maintain a geometry of the gastrointestinal device 100. In various examples, one or more of the suture tethers extend through one or more portions of the gastrointestinal device 100 and through one or more portions of the surrounding anatomy. Generally, the suture tethers thus operate as secondary anchoring mechanisms that help maintain a position of the gastrointestinal device 100 relative to the surrounding anatomy.

Turning now to FIGS. 4A and 4B, in some embodiments, a suture tether 200 is an anti-migration device that includes a body 202 having a first end 204, a second end 206 opposite the first end 204, and an elongate middle portion 208 extending between the first end 204 and the second end 206. The body 202 may be comprised of one or more filamentary members, a braided fiber, or may be a wire or a braided wire. That is, in some examples, the body 202 may be structurally compressible, while in other examples, the body 202 is unable to independently support a compressive load without significant deformation (e.g., folding or wrinkling). In various examples, the body 202 is resilient to tensile loads. In some examples, the body 202 is stretch resistant. It is to be appreciated that the body could be composed of bio-compatible non-absorbable suture materials as polypropylene, PTFE, ePTFE or dPTFE, polyester, nylon, UHMWPE or stainless steel. In some examples, the body 202 is formed of a material configured to resist tissue ingrowth such as polypropylene or nylon, dPTFE or stainless steel.

In various embodiments, the suture tether 200 includes one or more retaining tabs. For example, as shown in FIG. 4A, the suture tether 200 includes a first retaining tab 210 and a second retaining tab 212. The retaining tabs 210 and 212 operate to maintain a position of the suture tether 200 relative to the gastrointestinal device 100. For example, in some instances, the retaining tabs 210 and 212 operate to minimize the risk of the suture tether 200 decoupling from the gastrointestinal device 100, as discussed further below. Though a variety of retaining tabs are contemplated and may be utilized without departing from the spirit or scope of the disclosure, in some examples, the retaining tabs are formed from one or more tubes. In some examples, as discussed in greater detail below, the tubes are configured such that the body 202 can be received within and coupled with the tube. In some examples, the tube can be crimped to facilitate a couple between the retaining tab and the body 202. The retaining tabs may be formed from variety of biocompatible materials including, but not limited to, metallics such as stainless steel and Nitinol, and polymers such as polytetrafluoroethylene (PTFE), expanded polytetrafluoroethylene (ePTFE), polyether ether ketone (PEEK), ultra-high-molecular-weight polyethylene (UHMWPE), polyurethanes, polyesters, polyimide, nylon and polypropylene.

In some examples, the retaining tabs are integral with the body 202. In some such examples, the retaining tabs and the body 202 for a monolithic unit. In some examples, one or more of the retaining tabs are coupled to the body 202. In some examples, the body 202 terminates at or within a retaining tab at each of its respective ends. It will be appreciated that any suitable method may be employed to couple the retaining tabs to the body 202, including, but not limited to, clamping, gluing, pinning, tying, or utilizing one or more fastening means, as those of skill will appreciate. As shown, the retaining tabs 210 and 212 are crimped onto the body 202.

In various embodiments, the suture tether 200 is configured to transition from a delivery configuration to a deployed configuration such that the suture tether 200 can be delivered to a target region in a minimal profile and subsequently deployed (e.g., coupled with the gastrointestinal device 100) in a manner that minimizes a potential for the retaining tab to decouple from the gastrointestinal device 100. Generally, when transitioned to the deployed configuration, one or more of the retaining tabs of the suture tether 200 change shape and/or orientation relative to the body 202. In various examples, one or more of the retaining tabs 210 and 212 are coupled to the suture tether 200 such that the retaining tabs are biased to adopt the deployed configuration when unconstrained. Such a configuration provides that the one or more of the first and second retaining tabs 210 and 212 will adopt or otherwise naturally transition to the deployed configuration upon being deployed within the anatomy. In some examples, naturally transitioning to the deployed configuration upon deployment can be accomplished by creating a pre-formed bend in the body 202.

FIG. 4B shows the suture tether 200 in a partially deployed configuration to illustrate one non-limiting example of the first and second retaining tabs 210 and 212 in delivery and deployed configurations. Specifically, in FIG. 4B, the first retaining tab 210 is oriented in a deployed configuration, while the second retaining tab 212 is oriented in a delivery configuration. As shown, the orientation of the first retaining tab 210 is different than the orientation of the second retaining tab 212. In some examples, in the deployed configuration, the retaining tabs are oriented transverse to (or otherwise extends transverse to) the body 202. For example, as shown in FIG. 4B, the first retaining tab 210 (which is illustrated in the deployed configuration), extends transverse to the body 202. In some examples, in the delivery configuration, the retaining tabs extend generally along or in line with the body 202. For example, as show in FIG. 4B, the second retaining tab 212 (which is illustrated in the delivery configuration), extends generally along or in line with the body 202.

Additionally, as shown in FIG. 4A, the body 202 terminates into or is otherwise coupled to the retaining tabs 210 and 212 at a midsection thereof. For example, as shown in FIG. 4A, the body 202 terminates into the first retaining tab 210 at a midsection 218 between a first end 214 and a second end 216 of the first retaining tab 210. Accordingly, in various example, the retaining tabs are coupled to the body 202 such that two or more portions of the retaining tabs project away from the body 202. As shown in FIG. 4A, first end 214 and second end 216 extend or project away from the body 202 in the deployed configuration.

As mentioned above, the suture tether 200 maintains a minimal profile in the delivery configuration. In some examples, the retaining tabs include one or more features to help facilitate a minimal delivery profile. For example, as shown in FIG. 4A, the first retaining tab 210 includes a relief 220 formed in the first retaining tab 210 that is configured to accommodate the body of suture tether 200 in the delivery configuration. For instance, as shown in FIG. 4B, the body 202 is accommodated by the relief 220 in the second retaining tab 212 in the delivery configuration. As can be seen in FIGS. 4A and 4B, the relief 220 in each of the first retaining tab 210 and the second retaining tab 212 extends a length of less than a total length of each the first and the second retaining tabs 210, 212.

It will be appreciated that while the retaining tabs 210 and 212 are illustrated in the above-discussed embodiments and examples as changing orientation relative to the body 202, in various embodiments, the retaining tabs of the suture tether 200 may additionally or alternatively change size and/or shape when the suture tether 200 is transitioned from the delivery configuration to the deployed configuration. For example, in some instances, the retaining tabs are inflatable members. In some other examples, the retaining tabs are expandable members that expand from a delivery profile to a deployed profile. In some such examples, the retaining members are self-expanding. In some examples, the retaining tabs are disc-shaped. In some example, the retaining tabs include one or more petals that are configured to project away from the body 202 in the deployed configuration. It will be appreciated that any suitable configuration for the retaining members may be utilized provided that the retaining members transition to a deployed configuration that minimizes a potential for the retaining tabs to decouple from the gastrointestinal device 100.

FIG. 5 is the cross section view of FIG. 3, illustrated with a deployed suture tether 200. As shown, in various examples, the suture tether 200 is configured to extend from the proximal portion 130 of the gastrointestinal device 100 to the distal portion 132 of the gastrointestinal device 100. In some examples, the suture tether 200 is configured to penetrate one or more of the proximal and distal portions 130 and 132 of the gastrointestinal device 100, as well as one or more portions of the surrounding anatomy. As discussed in greater detail below, the suture tether 200 is deployed within the anatomy such that it penetrates the pyloric sphincter 26 (e.g., the muscle associate with the pylorus 20).

As shown in FIG. 5, the suture tether 200 penetrates the proximal portion 130 of the gastrointestinal device 100. In some examples, the suture tether 200 penetrates the proximal wall flange 148 of the proximal portion 130. In some examples, the second retaining tab 212 is positioned adjacent the proximal wall flange 148 on the stomach-side of the gastrointestinal device 100. That is, in various examples, the suture tether 200 is deployed such that the proximal wall flange 148 of the proximal portion 130 (or the proximal portion 130, generally) is situated between the second retaining tab 212 and the tissue of the pylorus 20 (e.g., the pyloric sphincter 26) sandwiched between the proximal and distal portions 130 and 132 of the gastrointestinal device 100.

Similarly, as shown in FIG. 5, the suture tether 200 penetrates the distal portion 132 of the gastrointestinal device 100. In some examples, the suture tether 200 penetrates the distal wall flange 150 of the distal portion 132. In some examples, the first retaining tab 210 is positioned adjacent the distal wall flange 150 on the duodenum-side of the gastrointestinal device 100. That is, in various examples, the suture tether 200 is deployed such that the distal wall flange 150 of the distal portion 132 (or the distal portion 132, generally) is situated between the first retaining tab 210 and the tissue of the pylorus 20 (e.g., the pyloric sphincter 26) sandwiched between the proximal and distal portions 130 and 132 of the gastrointestinal device 100.

In various examples, the suture tether 200 is deployed such that suture tether 200 spans between the proximal and distal portions 130 and 132 without penetrating the neck portion 134 of the gastrointestinal device 100. For example, as shown in FIG. 5, the suture tether 200 is deployed such that it penetrates each of the proximal and distal portions 130 and 132 to the gastrointestinal device 100 and spans therebetween without penetrating the neck portion 134 of the gastrointestinal device 100. Put differently, in various examples, the suture tether 200 is deployed and penetrates the gastrointestinal device 100 at one or more positions radially outward from the neck portion 134.

It will be appreciated that one or more suture tethers 200 may be utilized to secure the gastrointestinal device 100 to the surrounding anatomy. For instance, in some examples, three suture tethers 200 may be deployed to secure the gastrointestinal device 100 to the surrounding anatomy. In some such examples, the suture tethers 200 are generally evenly distributed about the gastrointestinal device 100. For example, where three suture tethers 200 are employed to secure the gastrointestinal device 100 to the surrounding anatomy, the suture tethers 200 each may be situated 120 degrees apart.

It will also be appreciated that such a configuration provides that the one or more suture tethers 200 will operate to minimize rotation of the gastrointestinal device 100 about a longitudinal axis of the gastrointestinal device 100 in-situ, as well as migration of the gastrointestinal device 100 relative to the pylorus 20.

It has been discovered that one of the factors contributing to dislodgment and migration of gastrointestinal implants (and those situated in the pylorus in particular) involves relative angulation of the portions of the gastrointestinal implants on either side of the pyloric sphincter 26 as a result of natural contractions and movements of the surrounding tissue. For instance, as an angulation of the distal portion 132 and/or the neck portion 134 increases relative to the proximal portion 130, the gastrointestinal device 100 deforms and loses its ability to adequately conform to the anatomy of the pylorus 20. This conformability issue results in a decrease in the surface area of the proximal portion 130 reacting against or otherwise engaging the anatomy of the pylorus 20 adjacent the proximal portion 130, thereby reducing the ability of the gastrointestinal device 100 to resist dislodgment and migration. Given a sufficient amount of angulation in combination with the natural contractions and movements of the surrounding anatomy, the effective surface area of the gastrointestinal device 100 will be insufficient to sustain retention of the gastrointestinal device 100 within the pylorus 20, and the gastrointestinal device 100 will become dislodged.

The suture tether 200 thus operates as a secondary anchoring mechanism that functions to minimize a relative angulation of the proximal and distal portions 130 and 132 (and/or the neck portion 134) relative to one another, and/or relative to the surrounding anatomy. The suture tether 200 physically secures the gastrointestinal device 100 to the surrounding anatomy by penetrating the surrounding anatomy and one or more of the proximal and distal portions 130 and 132 of the gastrointestinal device 100. In some such examples, the suture tether 200 operates to maintain a relative alignment of the anatomy and the portion of the gastrointestinal device 100 to which the suture tether 200 is coupled. In some examples, such a configuration operates to maximize and maintain the effective surface area of the gastrointestinal device 100 available for reacting against or otherwise engaging the surrounding anatomy to prevent dislodgment and/or migration.

In those configurations where the suture tether 200 extends through the surrounding anatomy and each of the proximal and distal portions 130 and 132 of the gastrointestinal device 100, the suture tether 200 additionally operates to minimize the amount of relative angulation between the proximal and distal portions 130 and 132 of the gastrointestinal device 100, thereby minimizing the amount of deformation of the gastrointestinal device 100. By further minimizing the amount of deformation of the gastrointestinal device 100 the suture tethers 200 operate to maximize and maintain the effective surface area of the gastrointestinal device 100 available for reacting against or otherwise engaging the surrounding anatomy to prevent dislodgment and/or migration.

In various examples, the amount to which the proximal and distal portions 130 and 132 are free to angulate relative to one another is based, at least in part, on a length of the suture tethers 200 relative to a distance between the proximal and distal portions 130 and 132, as those of skill will appreciate. In some examples, a length of the suture tether 200 (e.g., a distance between the first and second retaining tabs 210 and 212) exceeds a distance between proximal and distal wall flanges of a given gastrointestinal device such that the first and second retaining tabs 210 and 212 do not contact tissue when implanted or pinch the proximal and distal wall flanges of a given gastrointestinal device together. For instance, in some nonlimiting examples, a distance between proximal and distal wall flanges of a gastrointestinal device may be eleven millimeters, while a distance between the first and second retaining tabs 210 and 212 of the suture tether 200 a may be between fifteen and thirty millimeters. In some examples, selecting or configuring the suture tethers in such a manner helps avoid pressure necrosis, ulceration and other damage to the anatomy. Moreover, selecting or configuring the suture tethers to have a length that exceeds a distance between proximal and distal wall flanges of a given gastrointestinal device allows for the gastrointestinal device to dynamically adjust to the anatomy as the surrounding anatomy moves in association with digestive behavior. The longer a given suture tether 200 is in relation to the distance between the proximal and distal portions 130 and 132, the greater the amount of potential angulation between the proximal and distal portions 130 and 132. Some degree of angulation between the proximal and distal portions 130 and 132 may be desired. For instance, some degree of angulation between the proximal and distal portions 130 and 132 may provide for a gastrointestinal device 100 that more appropriately conforms to the surrounding anatomy.

Examples of suitable constructions of the gastrointestinal device 100 are illustrated and described in U.S. patent application Ser. Nos. 15/060,418, 14/872,990, and 15/600, 214, the contents of each of which are incorporated herein by reference. It will be appreciated that the gastrointestinal device 100 may be delivered according to methods known to those of skill in the art. Examples of suitable methods for delivering the gastrointestinal device 100 are illustrated and described in U.S. patent application Ser. Nos. 15/060,418, 14/872,990, and 15/600,214, mentioned above.

In various examples, the gastrointestinal device 100 may include one or more anchoring components that individually or collectively operate to maintain a position of the gastrointestinal device 100 within the patient's anatomy. In some examples, a sleeve 120 may be attached to the anchor 110, as those of skill will appreciate. It will also be appreciated that the gastrointestinal device 100 may be an implant, a gastrointestinal implant, or a pyloric implant.

In various embodiments, the gastrointestinal device 100 and the suture tethers 200 may be endoscopically implanted within and/or retrieved from the patient's anatomy while in a delivery configuration as discussed above. Generally, in the delivery configuration, the gastrointestinal device 100 and/or the suture tethers 200 are in a closed, compressed, or collapsed configuration in that they possess a smaller profile than a deployed profile, as will be appreciated.

Figure 6:
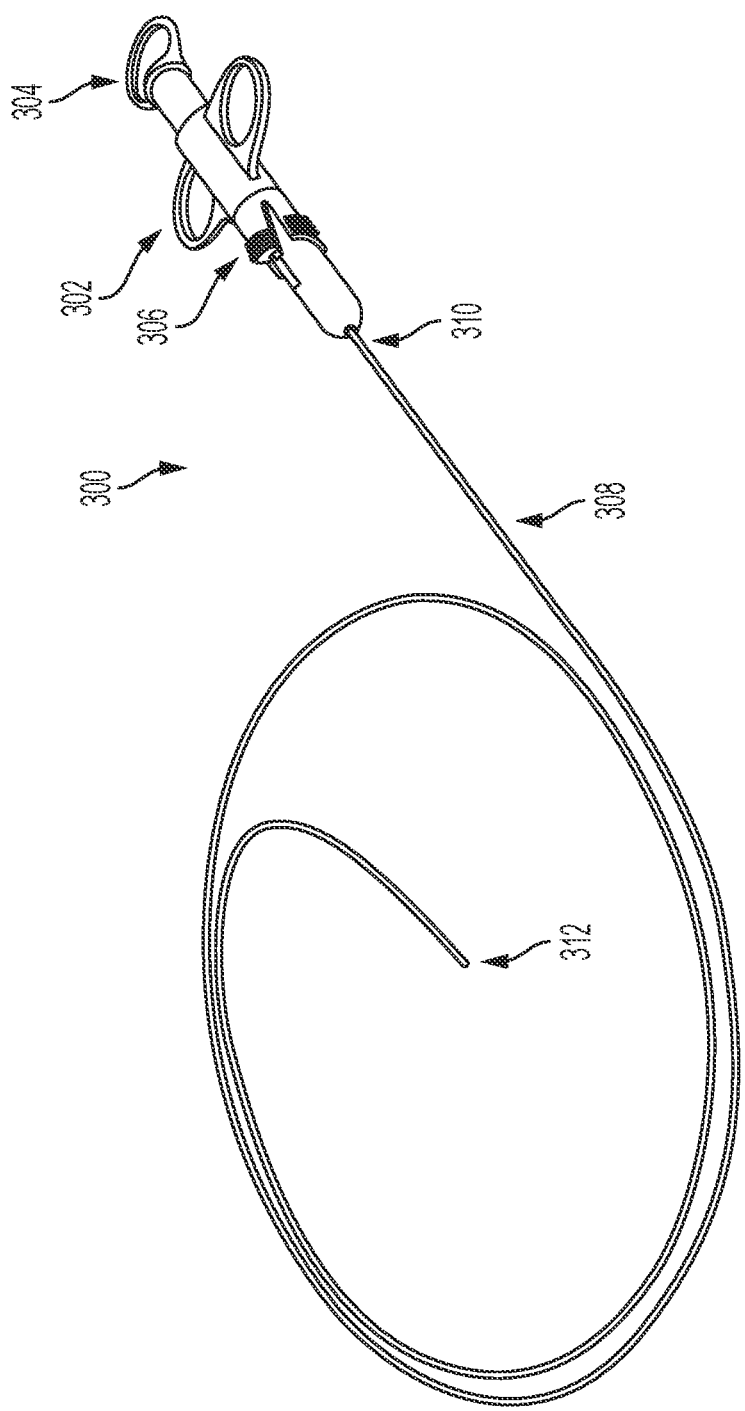
FIG. 6 is front perspective view of a delivery system, according to some embodiments.
Figure 7:
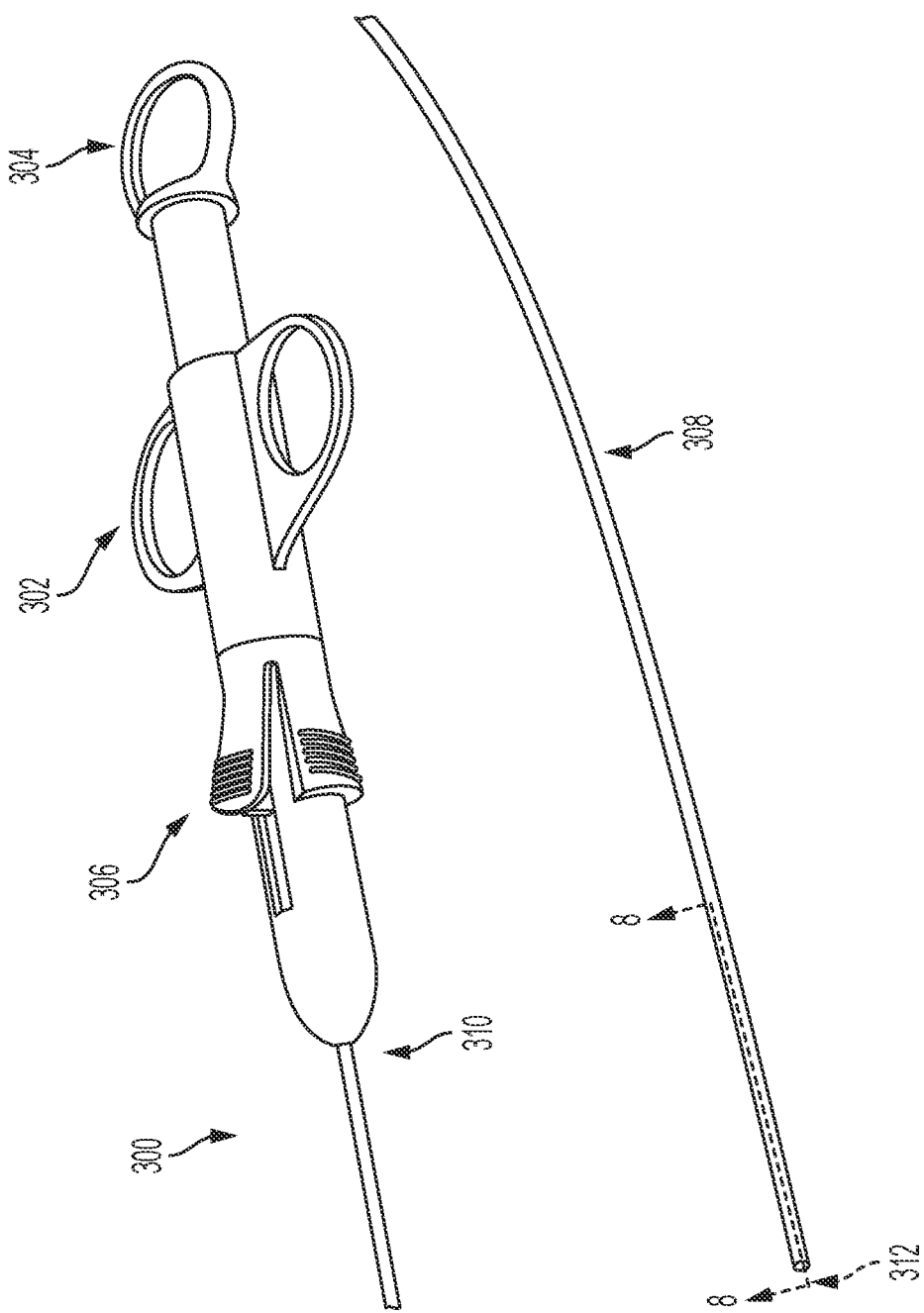
FIG. 7 is a magnified view of the delivery system of FIG. 6, according to some embodiments.

FIGS. 6 to 11 show a delivery system 300 and associated operation for delivering and deploying one or more of the suture tethers 200 to secure the gastrointestinal device 100 within the patient's anatomy. As shown in FIGS. 6 and 7, the delivery system 300 includes a handle 302 having a needle pushing element 304 and a suture tether pushing element 306. In various examples, the delivery system further includes an elongate element 308 having a proximal end 310 and a distal end 312. In some examples, the elongate element 308 is a catheter. In various example, the handle 302 is operable coupled with the elongate element 308. In some examples, the handle 302 is coupled to the proximal end 310 of the elongate element 308. It is to be appreciated that the various delivery systems discussed herein, including delivery system 300, may be delivered over one or more guidewires.

Figure 8:
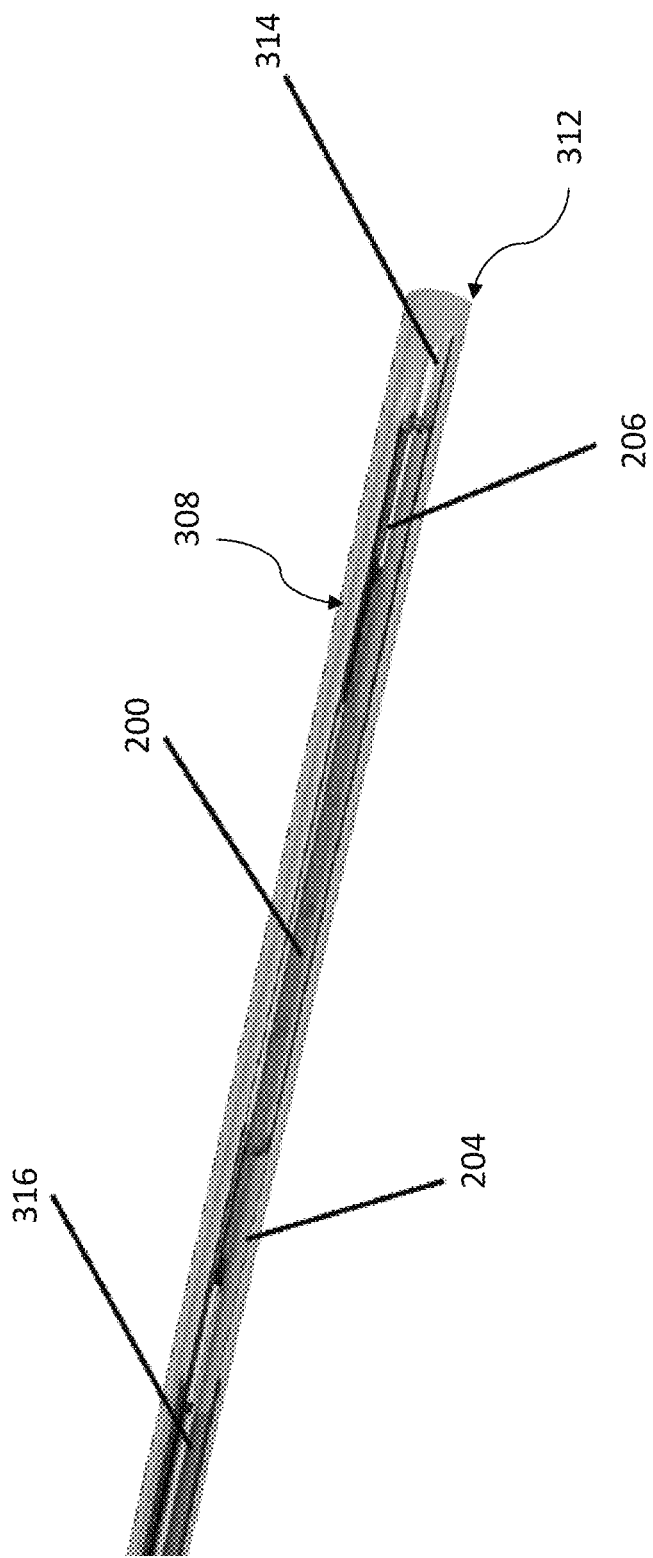
FIG. 8 is cross section view of a portion of the delivery system of FIG. 6 taken along line 8-8, according to some embodiments.

FIG. 8 is a cross section view of the distal end 312 of the elongate element 308 taken along line 8-8 of FIG. 7. As shown in FIG. 8, in various examples, the delivery system further includes a needle 314 and a suture tether pusher 316. In various examples, the suture tether pusher 316 and the needle 314 are each coaxially situated within the elongate element 308. Thus, in various examples, the elongate element 308 includes a lumen extending therethrough. In various examples, the needle 314 is coaxially received within the lumen of the elongate element 308. In some examples, the suture tether pusher 316 is coaxially received within a lumen of the needle 314.

As discussed in greater detail below, in some examples, the suture tether 200 is additionally situated within the lumen of the needle 314. In various examples, the needle 314 is operably coupled to the needle pushing element 304 of the handle 302. It will be appreciated that the needle 314 may be coupled with the needle pushing element 304 via any suitable means or mechanism, provided that an actuation of the needle pushing element 304 causes a corresponding actuation of the needle 314. In some examples, the needle 314 may be formed from a hollow elongate element having a proximal end and a distal end, wherein the hollow elongate element forming the needle 314 extends through the lumen of the elongate element 308. In some such examples, the proximal end of the elongate element forming the needle 314 is coupled to the needle pushing element 304, and the distal end of the elongate element forming the needle 314 is configured as a sharp tip suitable for piercing and driving through tissue. In some other examples, the needle 314 may be coupled to a member that extends through the elongate element 308. In various embodiments, the distal end of the needle 314 is rigid and long enough to hold the suture tether 200 in a collapsed configuration during its delivery. In some examples, the distal end of the needle 314 is coupled to a flexible shaft that extends back to the needle pushing element 304 in the handle. The properties of the needle 314 are such that the proximal section possesses sufficient flexibility to bend during navigation through the anatomy, while the distal portion possesses sufficient stiffness to allow the user to push the distal end of the needle through the target tissue. In some examples, the proximal section of the needle 314 may be constructed of a high durometer polymer, such as PEEK, Nylon, and polyurethane. The stiffer distal section of the needle may be made from stainless steel, Nitinol, or similar metals which are biocompatible and can be processed to include a sharp tip for piercing tissue. It is to be appreciated, however, that the full length of the needle 314 may be formed from a single piece of Nitinol, or a length of stainless steel tubing that has been modified in such a way as to make the proximal portion thereof sufficiently flexible to navigate the anatomy. In some such examples, the full length of the needle may be formed from a stainless steel tube that has been laser cut along a portion of its length (e.g., along the proximal portion) in a spiral configuration.

In various examples, an actuation of the needle pushing element 304 causes a corresponding actuation of the needle 314. When actuated, the needle 314 generally translates (e.g., proximally or distally) relative to the elongate element 308, as discussed in greater detail below. In some examples, the needle pushing element 304 can be actuated to transition the needle 314 between stowed and deployed states. In the stowed stated, the needle 314 is stowed within or otherwise concealed within the elongate element 308. That is, in the stowed stated, the distal tip of the needle 314 is positioned proximal to the distal end 312 of the elongate element 308. The stowed state generally corresponds with the needle pushing element 304 being proximally advanced to a delivery position. The delivery system 300 is shown in FIGS. 6 and 7 with the needle pushing element 304 positioned in the delivery position.

On the other hand, in the deployed state, the needle 314 extends from the distal end 312 of the elongate element 308 such that the distal tip of the needle is positioned distal to the distal end 312 of the elongate element 308. The deployed state generally corresponds with the needle pushing element 304 being distally advanced to a deployed position. As the needle pushing element 304 is transitioned from the delivery position to the deployed position (e.g., as the needle pushing element 304 is distally advanced), the needle 314 translates distally relative to the elongate element 308. That is, in various examples, a distal actuation of the needle pushing element 304 relative to the handle 302 and/or the elongate element 308 and/or the suture tether pushing element 306 causes a distal translation of the needle 314 relative to the elongate element 308.

Figure 9:
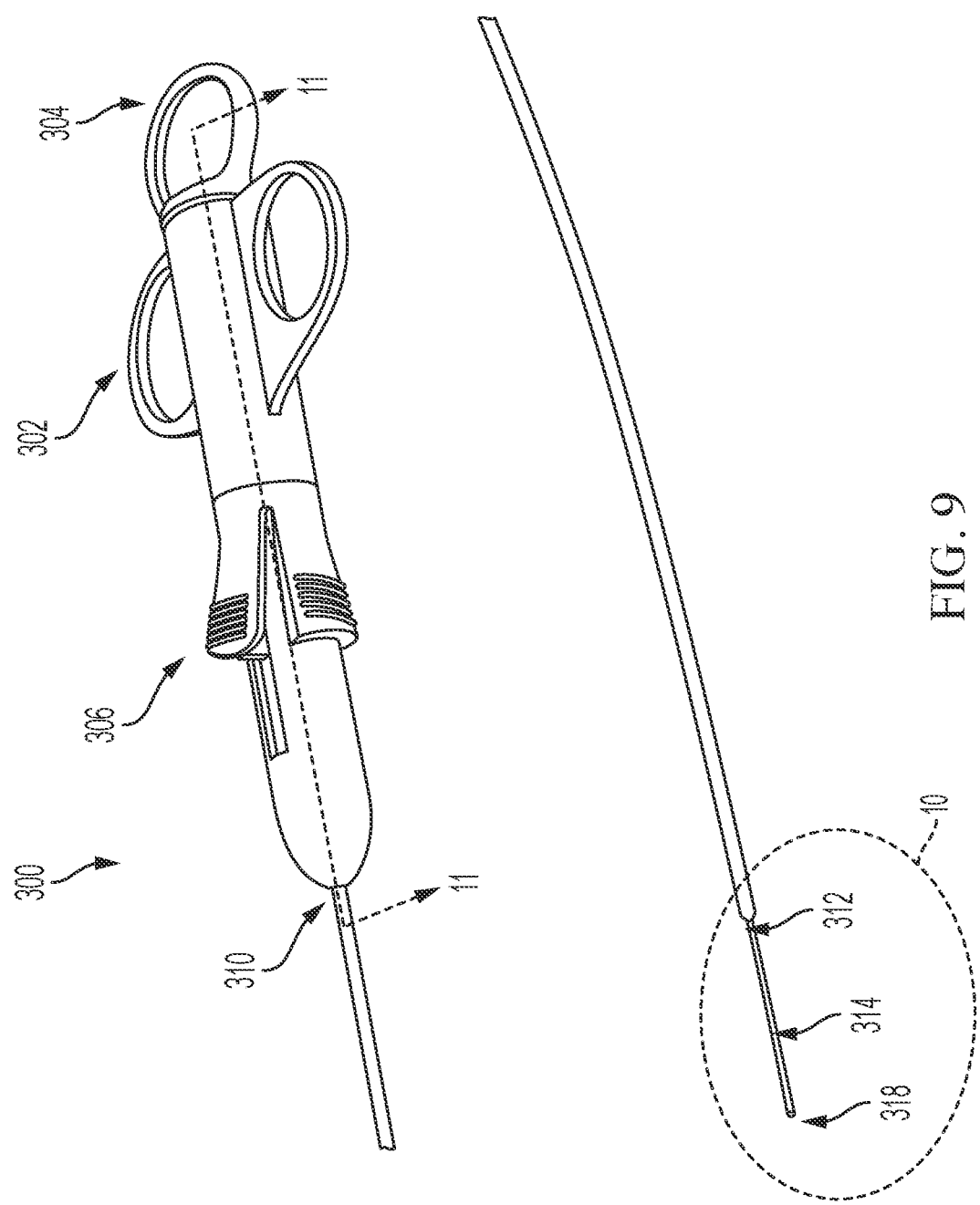
FIG. 9 is a magnified view of the delivery system of FIG. 6, according to some embodiments.
Figure 10:
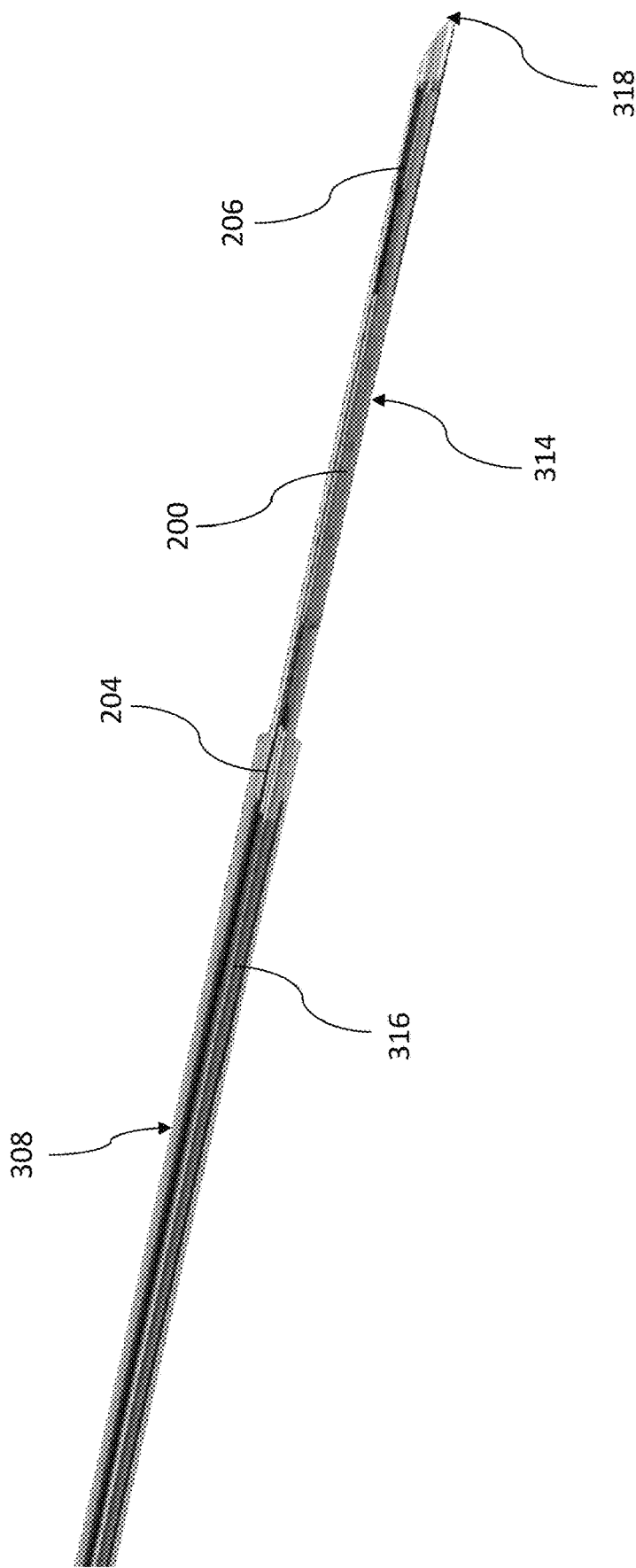
FIG. 10 is a magnified view of circle 10 of FIG. 9, according to some embodiments.

The delivery system 300 is shown in FIGS. 9 and 10 with the needle pushing element 304 positioned in the deployed position. For example, as shown in FIG. 9, the needle pushing element 304 has been distally advanced relative to the handle 302 and the suture tether pushing element 306. Additionally, as shown, the needle 314 has been distally advanced relative to the elongate element 308 such that a portion of the needle 314 is exposed. In particular, as shown, a distal tip or end 318 of the needle 314 is positioned distal to the distal end 312 of the elongate element 308.

Figure 11:
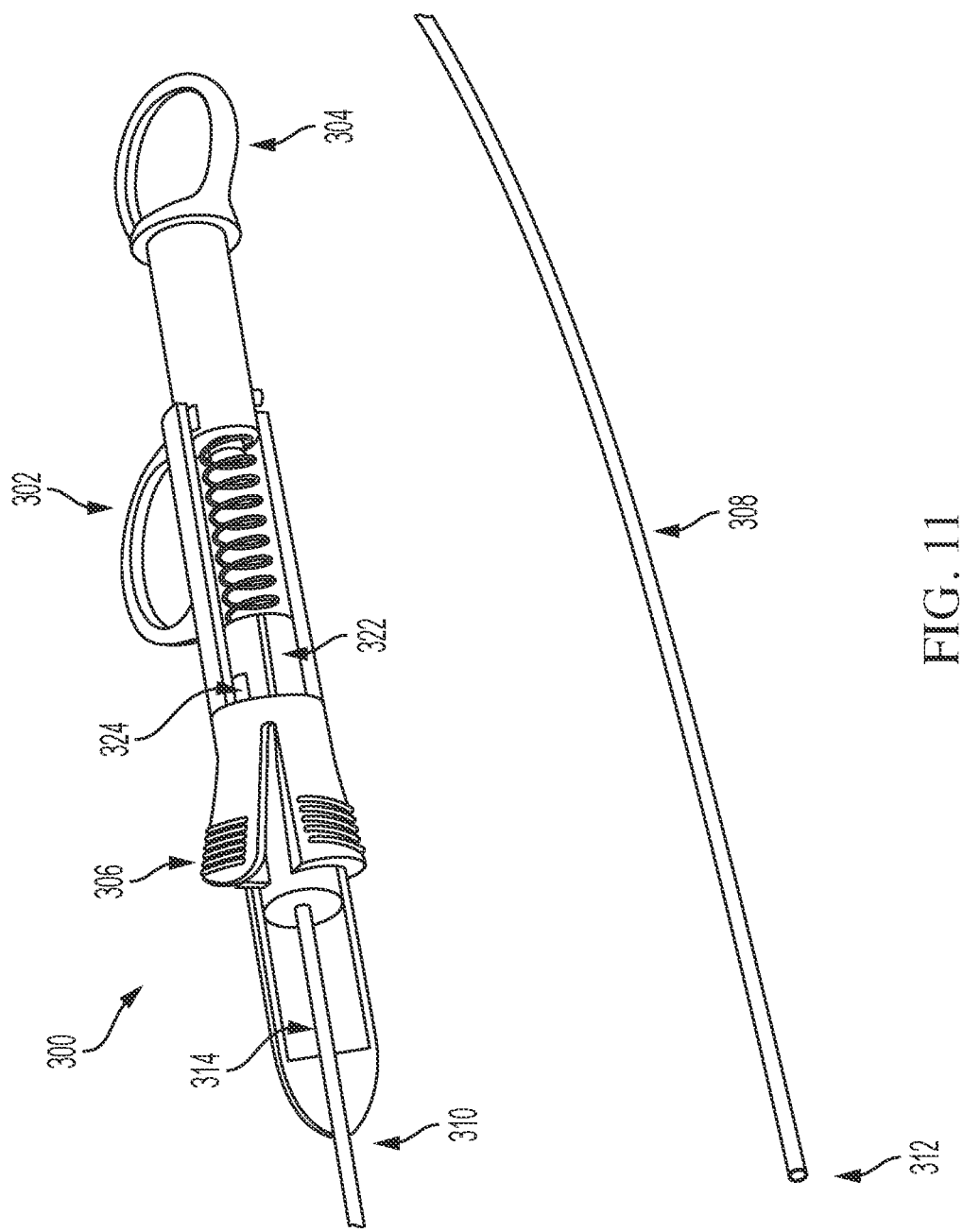
FIG. 11 is a magnified view of the delivery system of FIG. 6, according to some embodiments.

In some examples, advancement of the needle pushing element 304 additionally causes an advancement of the suture tether pusher 316. Such a configuration is facilitated by a deployment mechanism of the delivery system 300. That is, in various examples, the delivery system 300 includes a deployment mechanism 320 that is operable to cause concurrent movement of the suture tether pusher 316 and the needle 314. As discussed further below, the deployment mechanism 320 is further configured to facilitate independent actuation of the suture tether pusher 316 relative to the needle 314. FIG. 11 is a front perspective view of the delivery system 300 with a portion of the handle 302 removed to illustrate the deployment mechanism 320 and its various components. As shown, the deployment mechanism 320 includes a housing 322 and a slide member 324. The slide member 324 is configured to slide relative to the housing 322.

As shown, the proximal end of the needle 314 is coupled to the housing 322 of the deployment mechanism 320, while the proximal end of the suture tether pusher 316 is coupled to the slide member 324. Additionally, as shown, the needle pushing element 304 is operably coupled to a distal end of the housing 322. It will be appreciated, however, that the needle pushing element 304 may be coupled to any portion of the housing 322 and in any suitable manner without departing from the spirit or scope of the present application provided that an actuation of the needle pushing element 304 causes an actuation of the housing 322, which in turn causes an actuation of the needle 314 relative to the elongate element 308. Similarly, because the slide member 324 is situated within the housing 322, the slide member 324 is operable to translate with the housing 322. Accordingly, an actuation of the needle pushing element 304 causes the housing 322 and the slide member 324 to translate. This translation of the slide member 324 with the housing 322 causes concurrent translation of the needle 314 and the suture tether pusher 316, as those of skill will appreciate.

It will also be appreciated that because the suture tether pusher 316 is coupled to the slide member 324 and because the slide member 324 is operable to translate relative to the housing 322 and needle 314, the slide member 324 can be actuated to cause the suture tether pusher 316 to translate relative to the housing 322 and the needle 314. Thus, in addition to being actuated in association with an actuation of the housing 322, the suture tether pusher 316 can be further or additionally actuated in association with an actuation of the slide member 324 relative to the housing 322.

In various examples, the slide member 324 is operable to be advanced and retracted relative to the housing 322. Thus, in various examples, the suture tether pusher 316 is operable to be advanced and retracted relative to the needle 314. In particular, a distal advancement or translation of the slide member 324 relative to the housing 322 causes a corresponding distal advancement of the suture tether pusher 316 relative to the needle 314. It will be appreciated that various other mechanisms can be utilized to cause advancement and retraction of the suture tether pusher relative to the needle 314. Thus, the above-discussed examples should not be construed as limiting. Instead, it should be appreciated that those mechanisms and their equivalents that can be configured to cause both concurrent operation of the needle 314 and the suture tether pusher 316 and independent advancement and retraction of the suture tether pusher relative to the needle 314 fall within the spirit and scope of the present application. For example, configurations where a proximal translation of the slide mechanism relative to the housing 322 causes a distal advancement of the suture tether pusher 316 relative to the needle 314 falls within the spirit and scope of the present application.

In various examples, as mentioned above, the slide member 324 can be distally advanced relative to the housing 322 to cause the suture tether pusher 316 to advance distally relative to the needle 314. In some examples, as mentioned above, such distal translation of the suture tether pusher 316 relative to the needle 314 is operable to cause the suture tether 200 to be deployed or translated relative to the needle 314. Specifically, as discussed above, in various examples, the delivery system 300 is operable to deliver one or more suture tethers 200 to a treatment site within the anatomy. In some such examples, a suture tether 200 is loaded into the delivery system, advanced to the treatment site, and deployed. In some such examples, the suture tether 200 is loaded into the lumen of the needle 314 such that the suture tether 200 is situated distal to the distal end of the suture tether pusher 316. Thus, as the suture tether pusher 316 is distally advanced relative to the needle 314, so too is the suture tether 200.

In various examples, the suture tether pushing element 306 is operable to cause a corresponding actuation of the suture tether pusher 316, as discussed above. Specifically, when the suture tether pushing element 306 is actuated, the suture tether pusher 316 generally translates relative to the elongate element 308. In various examples, a proximal advancement or translation of the suture tether pushing element 306 corresponds with a proximal advancement or translation of the suture tether pusher 316. Similarly, in various examples, a distal retraction or translation of the suture tether pushing element 306 corresponds with a distal retraction or translation of the suture tether pusher 316. In some examples, similar to the needle pushing element 304, the suture tether pushing element 306 can thus be actuated to transition the suture tether pusher 316 between stowed and deployed states. In the stowed stated, the suture tether pusher 316 is stowed within or otherwise concealed within the lumen of the needle 314 such that a suture tether 200 can be placed within the needle 314 such that both the first and second ends 204 and 206 are situated proximal to the distal tip or end 318 of the needle 314. That is, in the stowed state, the distal tip of the needle 314 is positioned distal to the first and second ends 204 and 206 of the suture tether 200 and distal to the distal end of the suture tether pusher 316. The stowed state generally corresponds with the suture tether pushing element 306 being situated in a delivery position. This may include proximally advancing or retracting the suture tether pushing element 306 to the delivery position. The delivery system 300 is shown in FIGS. 9 and 11 with the suture tether pushing element 306 situated in the delivery position.

On the other hand, in the deployed state, the suture tether pusher 316 is distally advanced such that the second end 206 of the suture tether 200 is forced or ejected from the lumen of the needle 314. That is, in various examples, when the suture tether pushing element 306 is advanced to a deployed position, the suture tether 200 is only partially ejected from the lumen of the needle 314. In some examples, as the needle pushing element 304 is transitioned from the delivery position to the deployed position (e.g., as the needle pushing element 304 is distally advanced), the suture tether pusher 316 translates distally relative to the needle 314. This distal advancement or translation of the suture tether pusher 316 relative to the needle 314 causes the suture tether pusher 316 to engage the suture tether 200 stowed within the lumen of the needle 314 and cause the suture tether 200 to be advanced relative to the needle 314.

Figure 12:
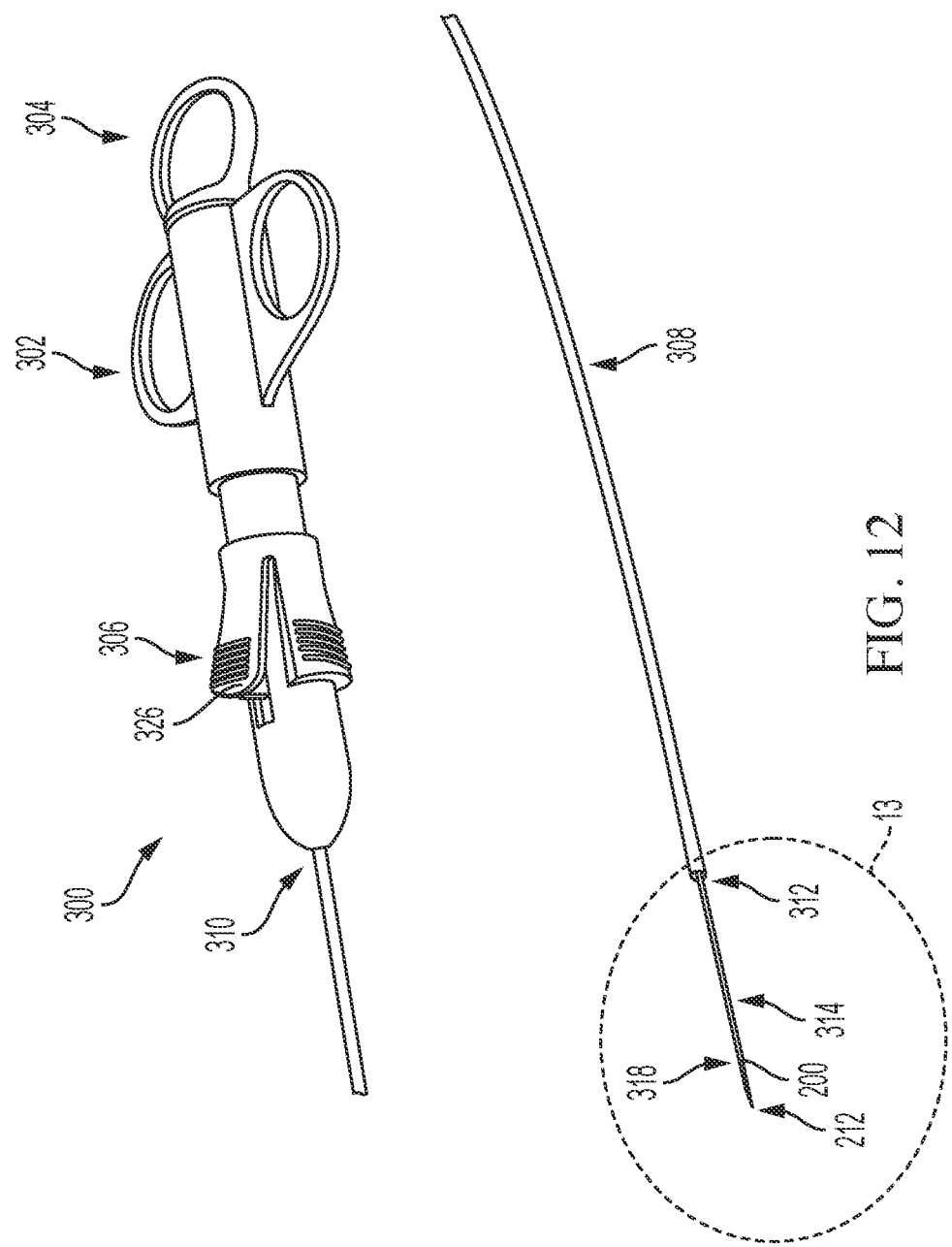
FIG. 12 is a magnified view of the delivery system of FIG. 6, according to some embodiments.
Figure 13:
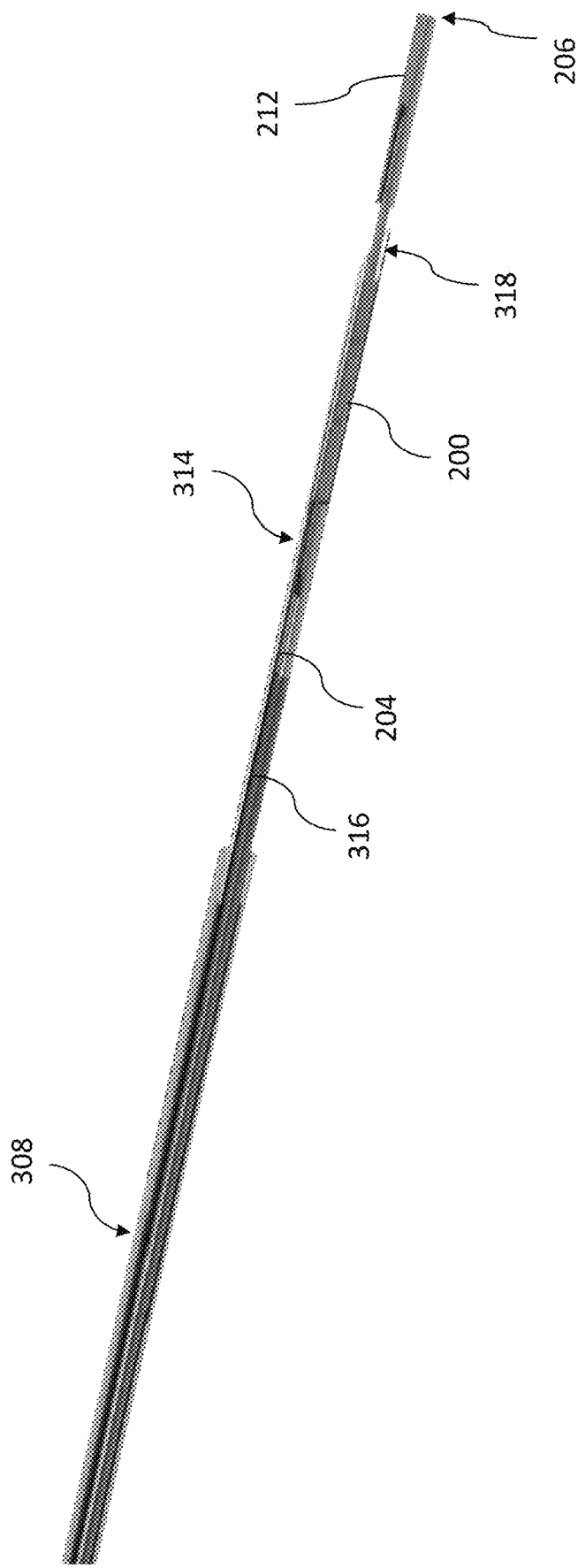
FIG. 13 is a magnified view of circle 13 of FIG. 12, according to some embodiments.

The delivery system 300 is shown in FIGS. 12 and 13 with the suture tether pushing element 306 positioned in the deployed position. Specifically, as shown in FIG. 12, the suture tether pushing element 306 and the slide member 324 have each been distally advanced relative to the handle 302 and the housing 322. As shown, the second end 206 of the suture tether 200 extends from the distal tip or end 318 of the needle 314. However, as shown, with the suture tether pushing element 306 positioned in the deployed position and with the needle pushing element 304 in the deployed position, a portion of the suture tether 200 (e.g., the first end 204) remains stowed within the lumen of the needle 314. As discussed in greater detail below, such a configuration provides that the needle 314 can be advanced through a tissue from a first side of the tissue to a second side of the tissue and the second end 206 of the suture tether 200 deployed on the second side of the tissue while maintaining the ability to deploy the first end 204 of the suture tether on the first side of the tissue.

In some examples, the delivery system 300 includes one or more features that operate to minimize a potential for unintended predeployment of the suture tether 200. Specifically, and with reference to FIGS. 9 and 12, the delivery system 300 is configured such that one or more tabs 326 of the suture tether pushing element 306 must be depressed before the suture tether pushing element 306 can be advanced distally relative to the handle 302. FIG. 9 shows the one or more tabs 326 of the suture tether pushing element 306 in a undepressed configuration, while FIG. 12 shows the one or more tabs 326 of the suture tether pushing element 306 in a depressed configuration.

Additionally, in some examples, the suture tether pushing element 306 cannot be depressed until the needle pushing element 304 is distally advanced or translated to the deployed position. In some such examples, the housing 322 includes one or more blocking features (not shown) that operate to prevent depression of the one or more tabs 326 of the suture tether pushing element 306 when the needle pushing element 304 is situated in the delivery position. However, upon advancing the needle pushing element 304 to the deployed position, and thereby distally advancing the housing 322 relative to the handle 302 and the suture tether pushing element 306, the one or more blocking features of the housing are advanced to a position where they no longer operate to prevent the one or more tabs 326 of the suture tether pushing element 306 from being depressed. In some examples, the housing additionally or alternatively includes one or more features that are configured to accommodate the one or more tabs 326 of the suture tether pushing element 306 such when the housing 322 is advanced in accordance with the needle pushing element 304 being distally advanced to the deployed position the features of the housing 322 configured to accommodate the one or more tabs 326 of the suture tether pushing element 306 are properly positioned relative to the suture tether pushing element 306 such that the one or more tabs 326 of the suture tether pushing element 306 can be depressed. Nonlimiting examples of such accommodation features include one or more slots, apertures, or reliefs in the housing 332.

Figure 14:
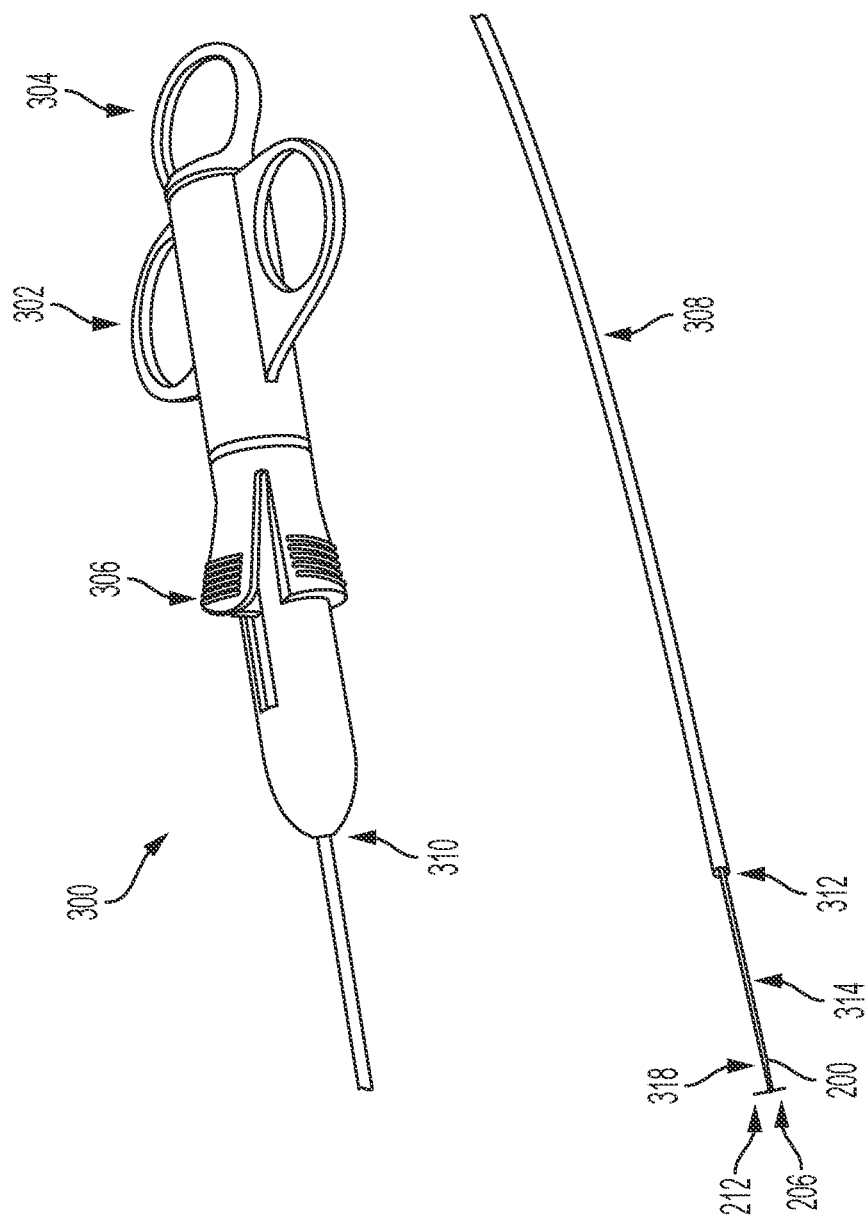
FIG. 14 is a magnified view of the delivery system of FIG. 6, according to some embodiments.

In some examples, after the suture tether 200 has been partially deployed from the distal end 318 of the needle 314, the suture tether pushing element 306 may be retracted or proximally advanced to the delivery position. When retracted to the delivery position, the suture tether pusher 316 is generally proximally withdrawn relative to the needle 314. FIG. 14 illustrates that suture tether pushing element 306 retracted to the delivery position with the second end 206 of the suture tether 200 deployed from the distal end 318 of the needle 314. It will be appreciated, that in various examples, the suture tether pushing element 306 need not be proximally withdrawn prior to deploying the remaining portions of the suture tether 200 from being deployed.

In various examples, after partially deploying the second end 206 of the suture tether 200, the needle pushing element 304 can be retracted or proximally withdrawn relative to the handle 302. In some examples, proximally withdrawing the needle pushing element 304 causes the needle 314 to be proximally withdrawn relative to the elongate element 308. In some examples, proximally withdrawing the needle pushing element 304 likewise causes the needle 314 to be proximally withdrawn relative to the suture tether 200 such that the suture tether 200 is entirely removed from the lumen of the needle 314. In some examples, the second retaining tab 212 operates to maintain a position of the suture tether 200 as the needle 314 is retracted or proximally withdrawn, as discussed in greater detail below.

Figure 15:
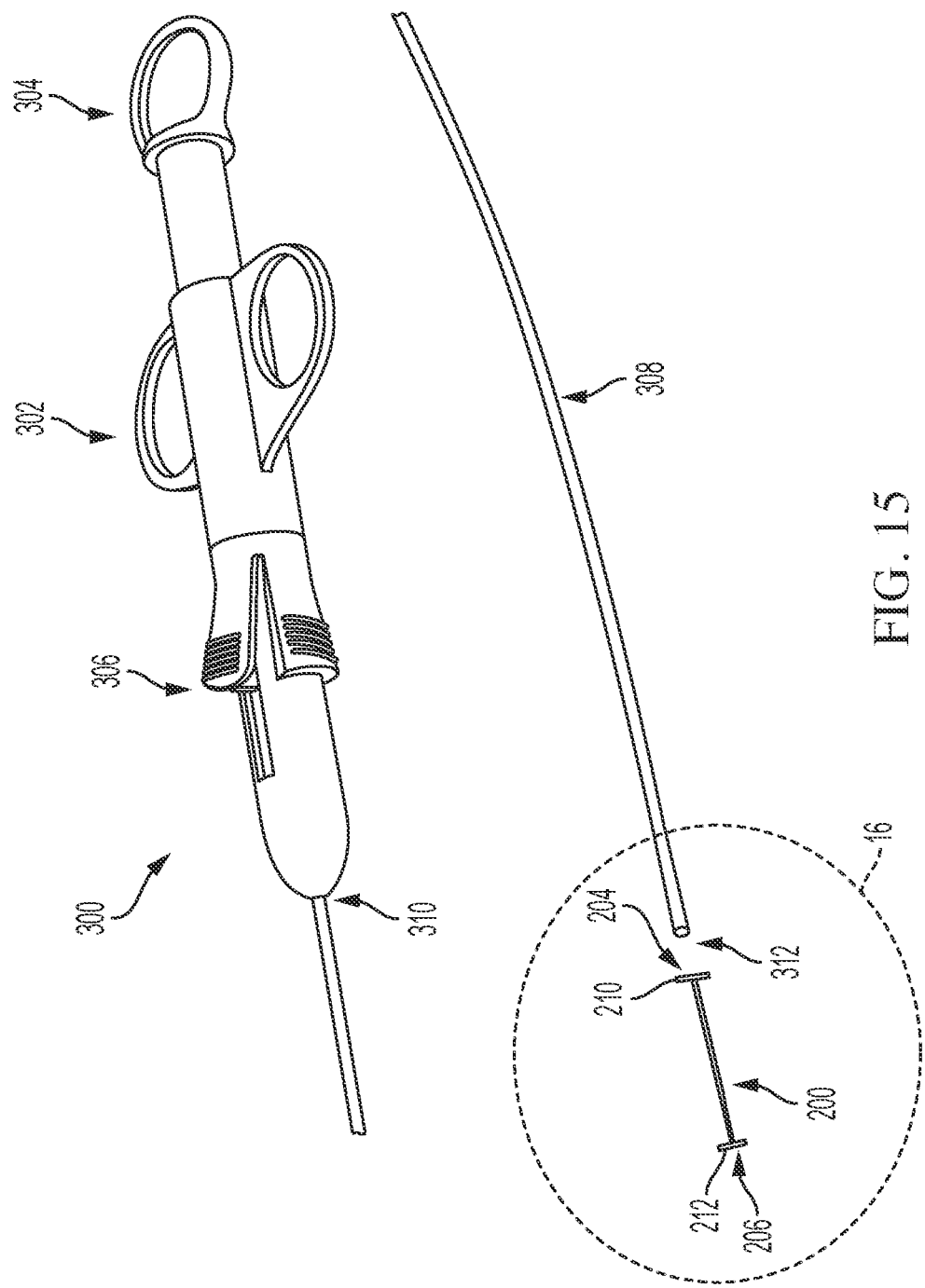
FIG. 15 is a magnified view of the delivery system of FIG. 6, according to some embodiments.
Figure 16:
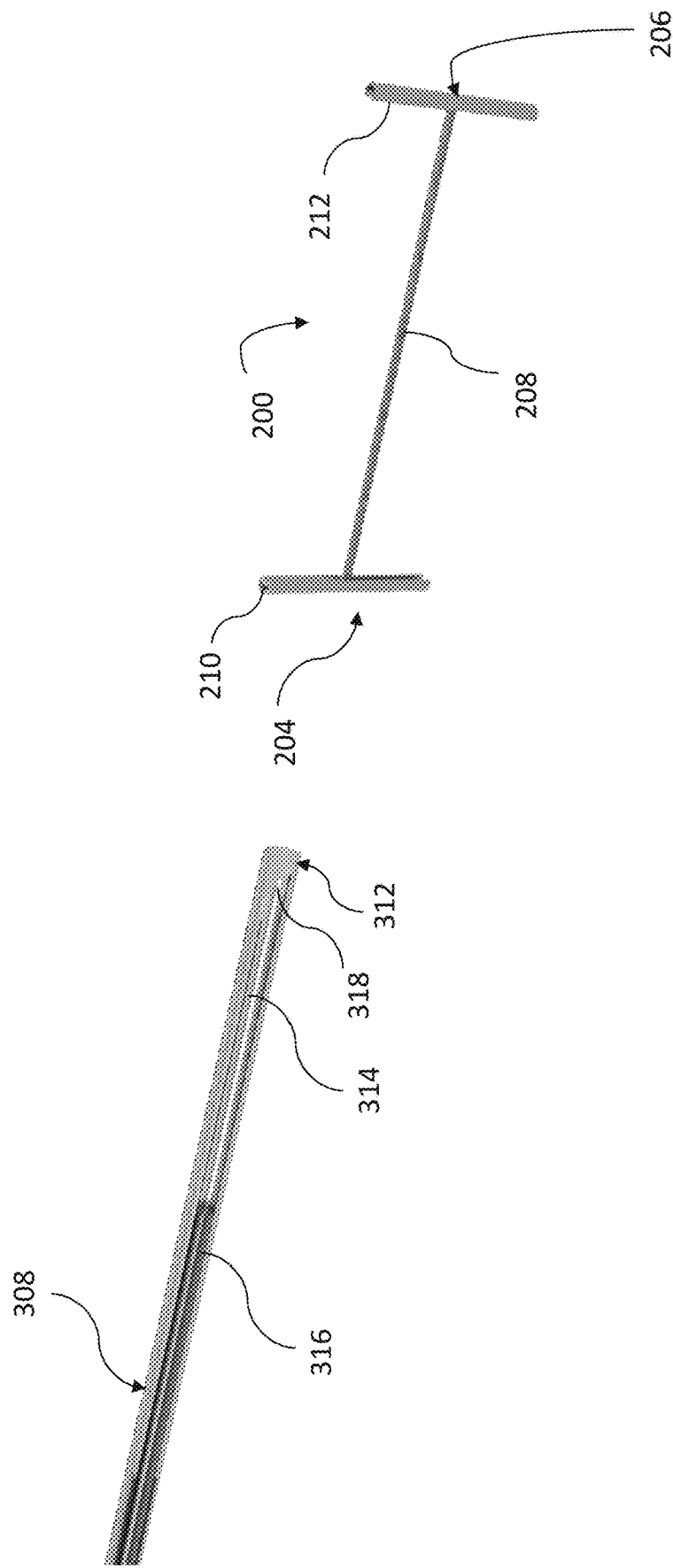
FIG. 16 is a magnified view of circle 16 of FIG. 15, according to some embodiments.

The delivery system 300 is shown in FIGS. 15 and 16 with the needle pushing element 304 retracted or proximally withdrawn back to the delivery position with the suture tether 200 completely deployed from the distal end 318 of the needle 314. When completely deployed, the first and second ends 204 and 206 of the suture tether 200 are ejected from or no longer situated within the lumen of the needle 314. In various examples, upon the distal end 318 of the needle 314 being proximally withdrawn or retracted to a position proximal to the first end 204 of the suture tether 200, the first retaining tab 210 is free to transition to the deployed configuration, as discussed above. As shown, the needle 314 has been proximally withdrawn or retracted relative to the elongate element 308 such the distal end 318 of the needle 314 is situated within the lumen of the elongate element 308 and proximal to the distal end 312 of the elongate element 308.

FIGS. 17 to 20 show a procedure for delivering and attaching suture tethers 200 to the patient's anatomy and the gastrointestinal device 100 to secure the gastrointestinal device 100 against dislodgment and/or migration. It will be appreciated that, in some embodiments, one or more components of the delivery system 300 are configured to fit within a working channel or lumen of a standard endoscope, as those of skill will appreciate. For instance, in some examples, the elongate element 308 is sized such that the elongate element may be inserted into a lumen of an endoscope and advanced therethrough. It will be appreciated that, in some examples the elongate element 308 is inserted into and advanced through the working lumen of an endoscope after the endoscope has been navigated through the patient's anatomy to the treatment site.

Figure 17:
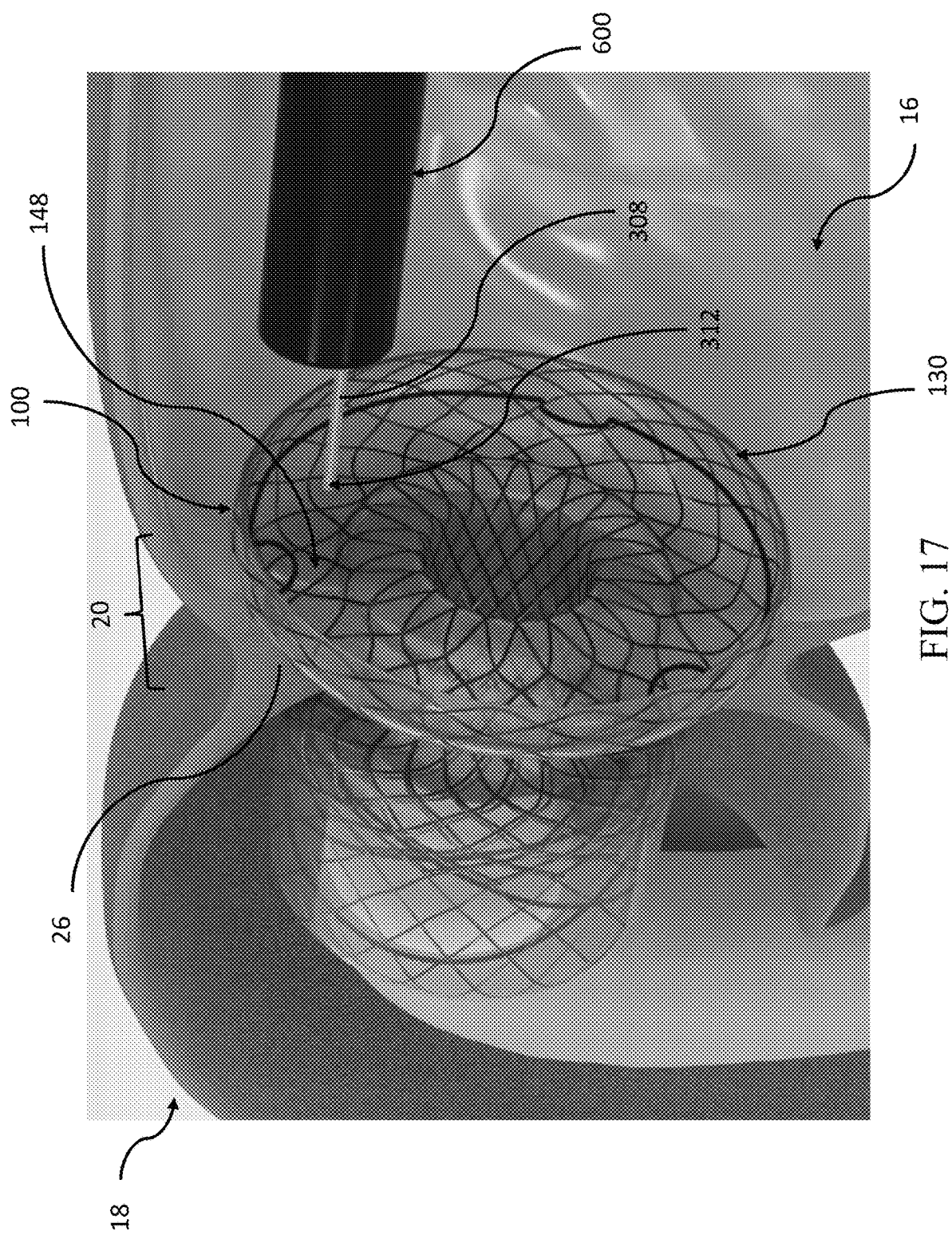
FIG. 17 is a cross-sectional view of a portion of the digestive tract in a human body with a gastrointestinal device positioned across the pylorus, according to some embodiments.

FIG. 17 shows the gastrointestinal device 100 described with reference to FIGS. 1 to 3 positioned within the body of a patient at the pylorus 20 between the stomach 16 and the intestine 18. The patient's anatomy has been sectioned in FIGS. 17 to 20 for clarity. In some instances, an endoscope 600 may be used to view the location of the gastrointestinal device 100. Additionally or alternatively, the tube of the endoscope 600 may also be used to guide the elongate element 308 toward the gastrointestinal device 100 and the locations selected for deploying the suture tethers. In some examples, as discussed in greater detail below one or more locator aids may be advanced to the treatment site and help guide the elongate element 308 toward the gastrointestinal device 100 and the locations selected for deploying the suture tethers, while helping maintain a position of the elongate element 308 relative to the gastrointestinal device 100 as the distal end 312 of the elongate element 308 is advanced through the gastrointestinal device 100 and the associated anatomy, and as the suture tether 200 is deployed. Moreover, as discussed further below, the suture tethers may be delivered via a delivery system entirely independently of an endoscope. That is, while an endoscope may be utilized to visualize the treatment region, delivery of the suture tethers 200 is accomplished via a delivery system that operates entirely independently of the endoscope.

Figure 18:
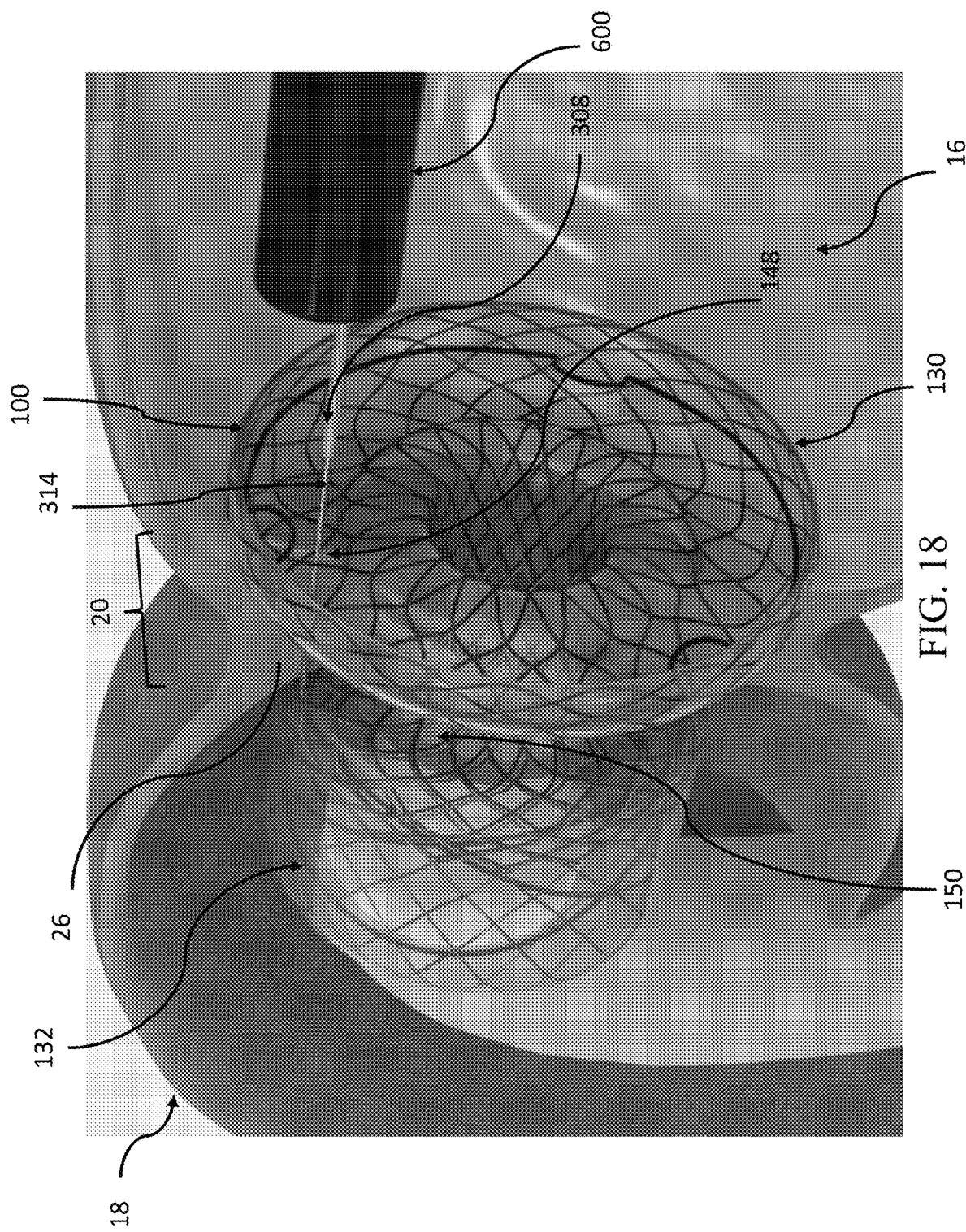
FIG. 18 is a cross-sectional view of a portion of the digestive tract in a human body with a gastrointestinal device positioned across the pylorus, according to some embodiments.
Figure 19:
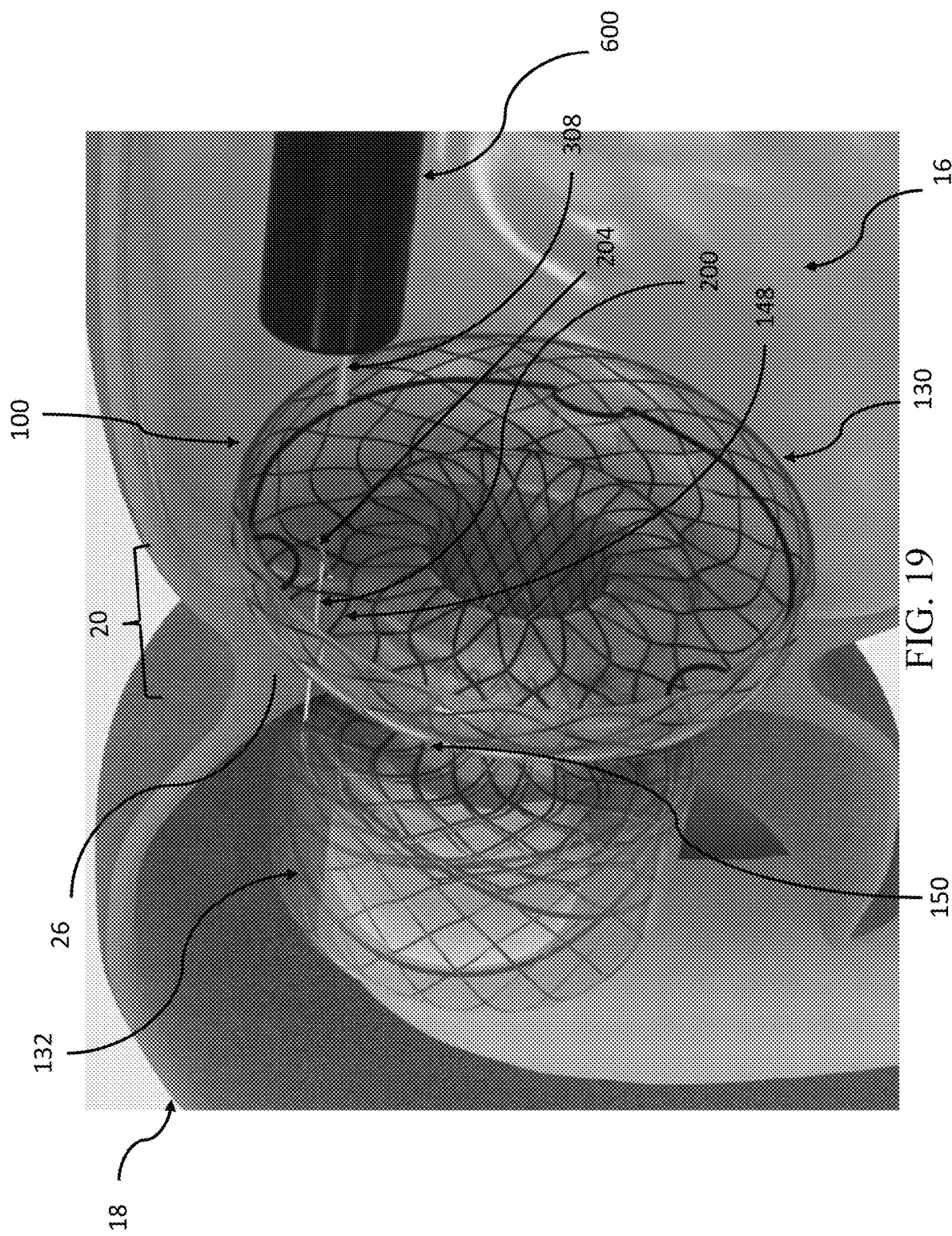
FIG. 19 is a cross-sectional view of a portion of the digestive tract in a human body with a gastrointestinal device positioned across the pylorus, according to some embodiments.

As shown in FIG. 17, the endoscope is positioned at approximately the twelve o'clock position with the distal end 312 of the elongate element 308 situated adjacent the proximal wall flange 148 of the proximal portion 130. FIG. 18 shows the needle 314 extending from the distal end 312 of the elongate element 308. The needle 314 has been distally advanced relative to the elongate element 308 such that the needle 314 extends through the proximal wall flange 148, through the pyloric sphincter 26, and through the distal wall flange 150. FIG. 19 shows a suture tether 200 delivered and deployed within the anatomy. It will be appreciated that the suture tether 200 is delivered and deployed in accordance with the description herein. In particular, as shown, the suture tether 200 extends through the proximal wall flange 148, through the pyloric sphincter 26, and through the distal wall flange 150 at the twelve o'clock position, such that the first retaining tab 210 is situated proximal to the proximal wall flange 148, and such that the second retaining tab 212 is situated distal to the distal wall flange 150.

As mentioned above, one or more locator aids may be advanced to the treatment site and help guide the elongate element 308 toward the gastrointestinal device 100 and the locations selected for deploying the suture tethers, while helping maintain a position of the elongate element 308 relative to the gastrointestinal device 100 as the distal end 312 of the elongate element 308 and/or the needle 314 is advanced through the gastrointestinal device 100 and the associated anatomy, and as the suture tether 200 is deployed. Thus, while the tube of an endoscope may be used to guide the elongate element 308 toward the gastrointestinal device 100 and the locations selected for deploying the suture tethers, in some examples, one or more additional delivery aids may be utilized in combination with the endoscope to accomplish delivery of the suture tethers 200.

Turning now to FIGS. 20A and 20B, a delivery system 400 includes a locator catheter 500 that is configured to operate with an endoscope 600 to help facilitate a delivery of the suture tethers 200 to a target treatment region. In various examples, the locator catheter 500 includes an elongate element 510, a locator capsule 520, and a hood 530. The locator capsule is situated at or proximate a distal end 512 of the elongate element 510, as shown. The hood 530 is situated proximal to the locator capsule 520, as shown. In some examples, the hood 530 is situated between the endoscope 600 and the locator capsule 520, as shown.

In various examples, the delivery system 400 is configured to interface with the endoscope 600. For instance, in some examples, the locator catheter 500 includes one or more endoscope engagement features 540, which are configured to constrain a radial position of the endoscope 600 relative to the locator catheter 500, as shown. By constraining a radial position of the endoscope 600 relative to the locator catheter 500, the delivery system 400 can help control or constrain a position of the elongate element 308 relative to the gastrointestinal device as the distal end 312 of the elongate element 308 and/or the needle 314 is driven through the gastrointestinal device and the adjoining anatomy during delivery of the suture tethers 200.

With continued reference to FIGS. 20A and 20B, the locator capsule 520 is configured to engage or otherwise interface with a gastrointestinal device that has been deployed within the anatomy. The engagement between the locator capsule 520 and the deployed gastrointestinal device helps maintain or constrain an orientation of the delivery system 300 while the suture tethers 200 are delivered and deployed. In some examples, the locator capsule 520 includes a body 522 that is shaped and sized in a manner that is complimentary to a shape and size of the deployed gastrointestinal device. For instance, in some examples, the body 522 is cylindrically shaped and configured to be received within a through-lumen of the deployed gastrointestinal device to cause engagement between the locator capsule 520 and the gastrointestinal device.

In some examples, the hood 530 is configured to accommodate the elongate element 308. For instance, as shown in FIG. 20A, during delivery of the suture tethers 200, the hood 530 is positioned between the endoscope 600 and the locator capsule 520 (and thus the deployed gastrointestinal device) such that the elongate element 308 extends through the hood 530 as it is advanced from the endoscope 600 toward the deployed gastrointestinal device. In some examples, the hood 530 includes an aperture or channel 532 that is configured to accommodate and constrain a radial position of the elongate element 308 when the elongate element 308 extends through the hood 530, as shown. It is to be appreciated that constraining radial positions of the endoscope 600 and/or the elongate element 308 relative to the locator capsule 520 (and thus the deployed gastrointestinal device) helps constrain the radial positions at which the suture tethers 200 are deployed. Thus, the delivery system 400 can be utilized to helps ensure that the suture tethers 200 are delivered through the pylorus tissue, and help minimize a risk that the wall of the stomach or small intestine are inadvertently punctured during the delivery procedure, and thus helps minimize a risk that the suture tethers 200 are delivered through the wall of the stomach or the small intestine, as mentioned above.

Additionally, as mentioned above, in various examples, a delivery system separate from the endoscope is configured to be advanced to the treatment region, and is configured to deliver and deploy the suture tethers 200. Turning now to FIGS. 21A-21E, a delivery system 700 is shown and includes a catheter 710 and a locator system 720. In some examples, the catheter 710 is a catheter and the locator system 720 is situated at or proximate a distal end 712 of the catheter 710. In some examples, the catheter 710 includes a through lumen for accommodating a guidewire (GW), as shown. It is to be appreciated that the delivery system 700 is illustrated in FIGS. 21A-21E without a corresponding gastrointestinal device or a surrounding anatomy to more clearly depict the elements and features of the delivery system 700. Operation of the delivery system 700 with a gastrointestinal device and/or within an anatomy is shown and described below in relation to at least FIGS. 23A-24B.

In various examples, the locator system 720 is configured to engage or otherwise interface with a gastrointestinal device that has been deployed within the anatomy. The engagement between the locator system 720 and the deployed gastrointestinal device helps maintain or constrain an orientation of the delivery system 700 while the suture tethers 200 are delivered and deployed. In some examples, the locator system 720 includes a locator capsule 722 that has a body that is shaped and sized in a manner that is complimentary to a shape and size of the deployed gastrointestinal device, much like that of the locator capsule 520 mentioned above. Thus, in some examples, the locator capsule 722 may be cylindrically shaped and configured to be received within a through-lumen of the deployed gastrointestinal device to cause engagement between the locator capsule 722 and the gastrointestinal device. It is to be appreciated, however, that the locator capsule 722 may be configured to interface with or engage the deployed gastrointestinal device in a number of other suitable manners, provided that the engagement between the locator capsule 722 and the gastrointestinal device operates to maintain or constrain an orientation of the delivery system 700 while the suture tethers 200 are delivered and deployed.

In some examples, the locator system 720 further includes a plurality of extendable arms, including a first extendible arm 724 and a second extendible arm 726 that can be selectively deployed to help facilitate a delivery of the suture tethers 200. In various examples, the first and second extendible arms 724 and 726 are longitudinally spaced apart from one another such that a gap is defined between the first and second extendible arms 724 and 726 when the first and second extendible arms 724 and 726 are radially extended from the locator capsule 722. For instance, as shown the first extendable arm 724 is situated more proximate a distal end 721 of the locator capsule 722 than is the second extendable arm 726. Likewise, as shown, the second extendable arm 726 is situated more proximate a proximal end 723 of the locator capsule 722 than is the first extendable arm 724. As discussed further below, the gap between the first and second extendable arms 724 and 726 is configured such that the first and second extendable arms 724 and 726 can straddle a neck portion of the gastrointestinal device so that the first extendable arm 724 is positioned distal to a distal wall flange of the gastrointestinal device while the first extendable arm 724 is positioned proximal to the proximal wall flange of the gastrointestinal device. As discussed further below, such a configuration helps maintain a longitudinal and a radial position of the delivery system 700 during delivery and deployment of the suture tethers 200.

Additionally, as shown, the locator system 720 is configured such that the first and second extendable arms 724 and 726 are operable to be selectively radially extended from the locator capsule 722. Thus, it is to be appreciated that such a configuration provides that the delivery system 700 is transitionable between a delivery configuration (e.g., where the first and second extendable arms 724 and 726 are stowed within the locator capsule 722) and a deployment configuration (e.g., where the first and second extendable arms 724 and 726 radially project from the locator capsule 722). A configuration including the first and second extendable arms 724 and 726 helps provide that the delivery system 700 maintains a minimal delivery profile.

Figure 21A:
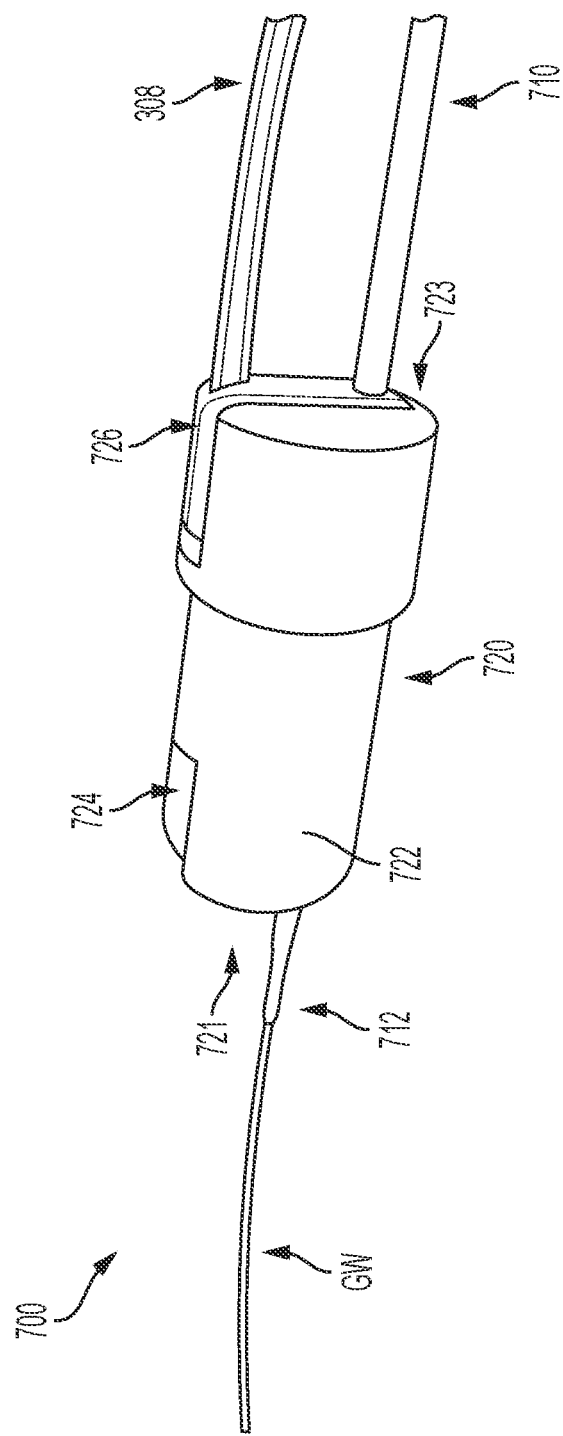
FIGS. 21A-21E illustrate a gastrointestinal implant delivery system, according to some embodiments
Figure 21B:
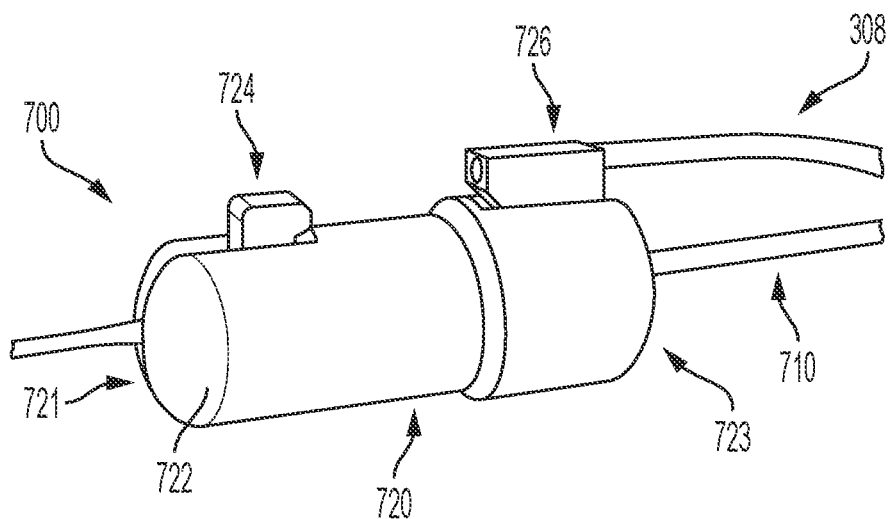
Figure 21C:
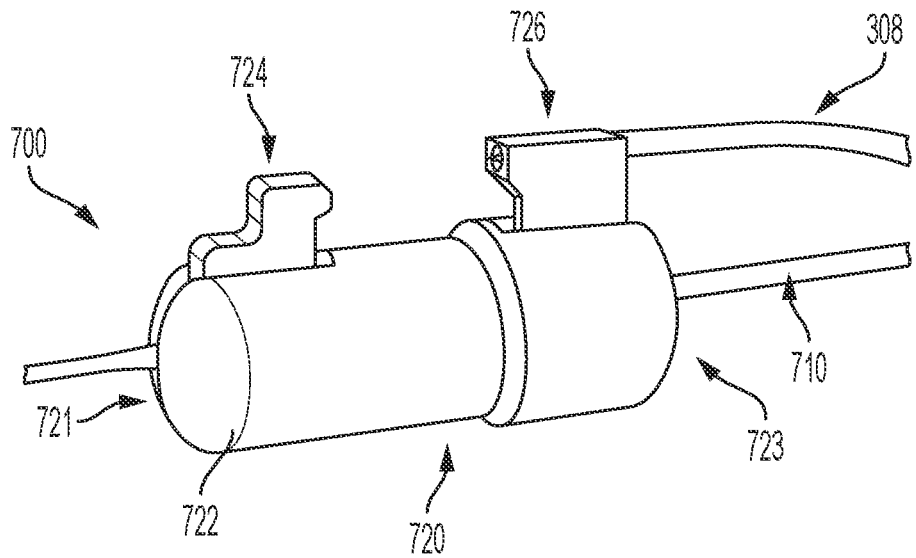

FIGS. 21A-21C illustrate a deployment sequence of the first and second extendable arms 724 and 726. FIG. 21A shows the delivery system 700 in a delivery configuration where the first and second extendable arms 724 and 726 are stowed within the locator capsule 722. FIG. 21B shows the first and second extendable arms 724 and 726 partially radially extended. FIG. 21C shows the delivery system 700 in a deployed configuration where the first and second extendable arms 724 and 726 are fully radially extended. In various examples, the delivery system 700 is configured to include the elongate element 308. For instance, as shown in FIGS. 21A-21E, the elongate element 308 is coupled to the second extendable arm 726 of the locator system 720. This coupling between the elongate element 308 and the locator system 720 helps constrain a position of the elongate element 308 (and thus the needle 314) relative to the locator system 720 during the delivery of the suture tethers 200. Thus, in the delivery configuration shown in FIG. 21A, the elongate element 308 is situated in a first radial position relative to the locator capsule 722 (e.g., a longitudinal axis of the elongate element 308 at the second extendable arm 726 is in a first radial position relative to a longitudinal axis of the locator capsule 722). In this first radial position, the elongate element 308 is misaligned with a target location for where the suture tether 200 is to extend through the gastrointestinal implant. On the other hand, in the deployed configuration shown in FIG. 21C, the elongate element 308 is situated in a second radial position relative to the locator capsule 722 (e.g., the longitudinal axis of the elongate element 308 at the second extendable arm 726 is in a second radial position relative to the longitudinal axis of the locator capsule 722). In some examples, the second radial position is a radial position that is more radial distant from the longitudinal axis of the locator capsule 722 than is the first radial position. In this second radial position, the elongate element 308 is properly aligned with the target location for where the suture tether 200 is to extend through the gastrointestinal implant.

Moreover, as mentioned above, the locator capsule 722 is configured to engage the deployed gastrointestinal device to help constrain a position of the locator system 720 relative to the gastrointestinal device during delivery and deployment of the suture tethers 200. Thus, it is to be appreciated that the coupling between the elongate element 308 and the locator system 720 helps constrain a position the needle 314 relative to the gastrointestinal device during the delivery and deployment of the suture tethers 200.

Figure 21D:
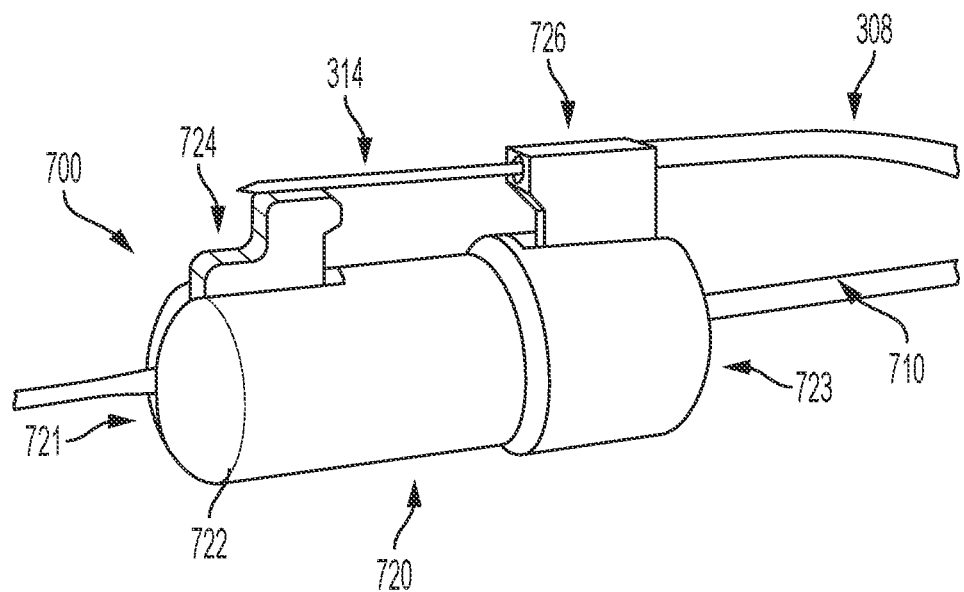
Figure 21E:
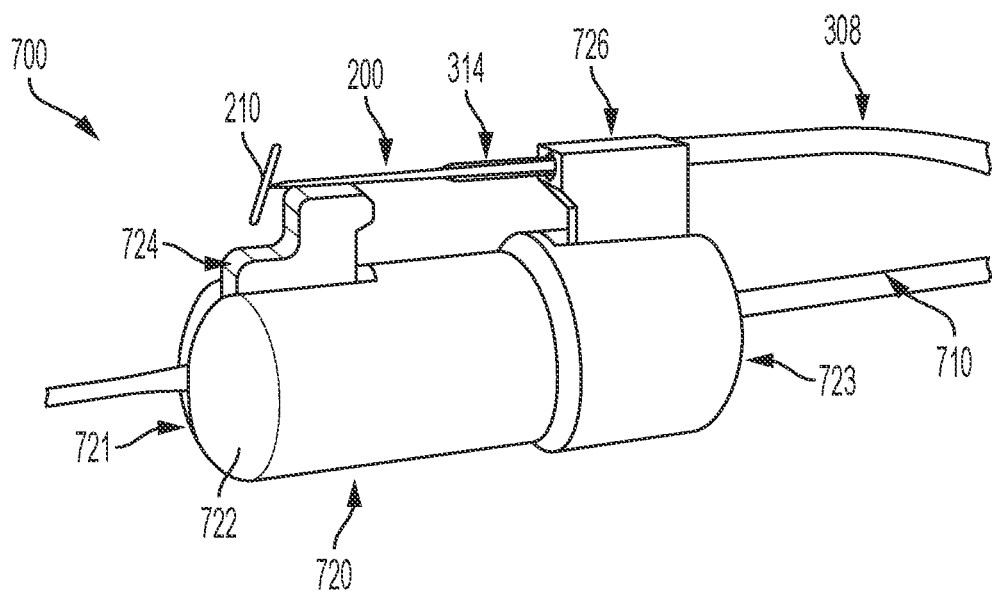

FIGS. 21D-21E illustrate an advancement of the needle 314 and a deployment of the suture tether from the elongate element 308. FIG. 21D shows the needle 314 advanced from the elongate element 308 such that the needle 314 extends across the gap between the first and second extendable arms 724 and 726. FIG. 21E shows the needle 314 partially retracted to reveal the suture tether 200 with the first retaining tab 210 of the suture tether 200 deployed. Thus, as shown in FIGS. 21D and 21E, the delivery system 700 is configured such that the needle 314 (and thus the suture tether 200) can be advanced across the gap between the first and second extendable arms 724 and 726, and thus is configured such that the needle 314 (and thus the suture tether 200) can be advanced from a position proximal to the proximal wall flange of a deployed gastrointestinal device to a position distal to the distal wall flange of the deployed gastrointestinal device.

In various examples, the first and second extendable arms 724 and 726 are selectively actuatable by a user, such as by way of a delivery handle from outside the body (e.g., handle 302). In some examples, as the first and second extendable arms 724 and 726 radially extend from the locater capsule 722, a relative distance between the first and second extendable arms 724 and 726 decreases. For example, as shown in FIGS. 21B and 21C, a relative distance between the first and second extendable arms 724 and 726 decreases from the position of the first and second extendable arms 724 and 726 shown in FIG. 21B to the position of the first and second extendable arms 724 and 726 shown in FIG. 21C. Thus, in some examples, the gap between first and second extendable arms 724 and 726 decreases as the first and second extendable arms 724 and 726 are deployed. In some examples, the first extendable arm 724 is configured to translate toward the second extendable arm 726 as the first and second extendable arms 724 and 726 are radially extended from the locator capsule 722. In some examples, the second extendable arm 726 is configured to translate toward the first extendable arm 724 as the first and second extendable arms 724 and 726 are radially extended from the locator capsule 722.

Figure 22:
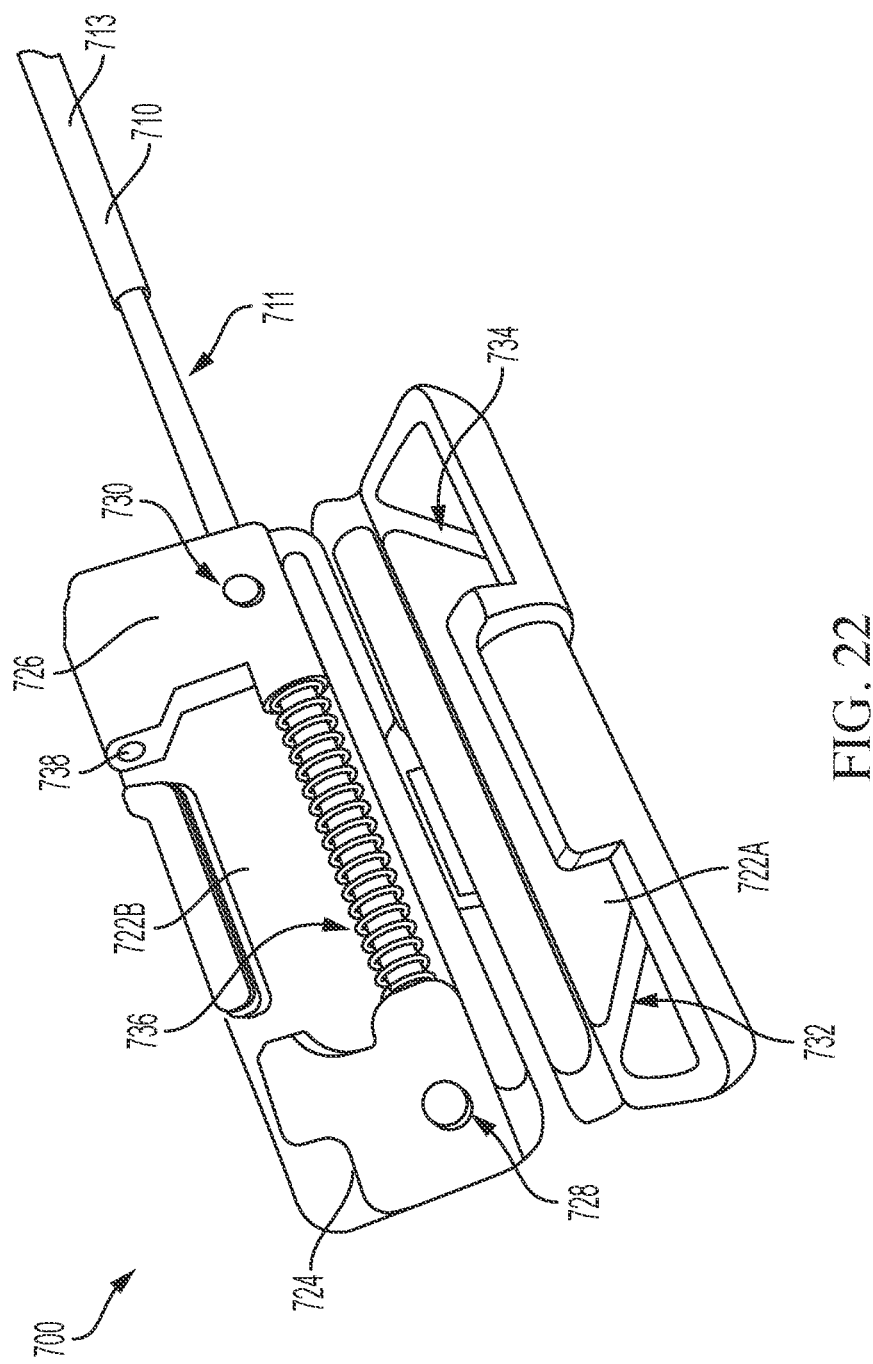
FIG. 22 illustrates a gastrointestinal implant delivery system, according to some embodiments

Turning now to FIG. 22, the delivery system 700 is shown with the locator capsule 722 split into two halves (722A and 722B) to reveal a nonlimiting exemplary internal configuration of locator capsule 722 and the first and second extendable arms 724 and 726. It is to be appreciated that the elongate element 308 has been removed for clarity (and is to be understood as being coupleable to the second extendable arm 726). As shown, the first extendable arm 724 includes a body having a protrusion 728. Although not shown, it is to be appreciated that the first extendable arm 724 may include a similar protrusion on an opposing side of its body. Similarly, as shown, the second extendable arm 726 includes a body having a protrusion 730, and may include a similar protrusion on an opposing side of its body (not shown).

Moreover, as shown, a first half 722A of the locator capsule 722 includes a plurality of grooves or channels, including a first channel 732 and a second channel 734. Although not shown (due to the presence of the first and second extendable arms 724 and 726), it is to be appreciated that the second half 722B of the locator capsule 722 may include a plurality of grooves or channels similar in size, shape, and position to the first and second channels 732 and 734 of the first half 722A of the locator capsule 722. As shown, the first and second channels 732 and 734 are angled relative to a longitudinal axis of the locator capsule 722 (e.g., coaxial with a longitudinal axis of a deployed gastrointestinal implant when the locator capsule 722 is engaged with the gastrointestinal implant). In some examples, the longitudinal axis of the locator capsule 722 is parallel with a longitudinal axis of the catheter 710. Though shown at approximately forty five degrees relative to the longitudinal axis of the locator capsule 722, it is to be appreciated that at least one of the first and second channels 732 and 734 may be angled at virtually any angle between zero degrees and ninety degrees. As discussed further below, the relative angle between the first and second channels 732 and 734 provides that the first and second extendable arms 724 and 726 radially extend from the locator capsule 722 as they translate relative to one another. Thus, the first and second channels 732 and 734 may be angled less than forth five degrees or alternatively more than forty five degrees. As those of skill in the art will appreciate, a first one of the extendable arms 724 and 726 may be angled at zero or ninety degrees provided that the other of the extendable arms 724 and 726 is angled at an angle different from zero and ninety degrees.

In various examples, the first channel 732 is configured to receive the protrusion 728 of the first extendable arm 724 such that the protrusion 728 of the first extendable arm 724 travels within and is otherwise constrained by the channel 732. This relationship between the protrusion 728 and the first channel 732 provides that the first extendable arm 724 radially extends from the locator capsule 722 as the first and second extendable arms 724 and 726 translate relative to one another. Similarly, the second channel 734 is configured to receive the protrusion 730 of the second extendable arm 726 such that the protrusion 730 of the second extendable arm 726 travels within and is otherwise constrained by the channel 734. This relationship between the protrusion 730 and the channel 734 provides that the second extendable arm 726 radially extends from the locator capsule 722 as the first and second extendable arms 724 and 726 translate relative to one another.

As mentioned above, in various examples, the locator capsule 722 is coupled to the catheter 710. In some examples, the catheter 710 includes a first elongate element 711 and a second elongate element 713. In some examples, the first elongate element 711 extends through a lumen of the second elongate element 713, as shown, such that the first and second elongate elements 711 and 713 can be moved relative to one another. In some examples, the first elongate element 711 is coupled to the first extendable arm 724, while the second elongate element 713 is coupled to one or more of the second extendable arm 726 and the locator capsule 722. Thus, it is to be appreciated that the first and second elongate elements 711 and 713 can be actuated relative to one another (such as by way of handle 302) to cause relative movement between the first and second extendable arms 724 and 726. For instance, the first elongate element 711 may be proximally withdrawn while the second elongate element 713 is held stationary to cause the first and second extendable arms 724 and 726 to be drawn closer to one another. Alternatively, the first elongate element 711 may be proximally withdrawn while the second elongate element 713 is distally advanced to cause the first and second extendable arms 724 and 726 to be drawn closer to one another.

Figure 23B:
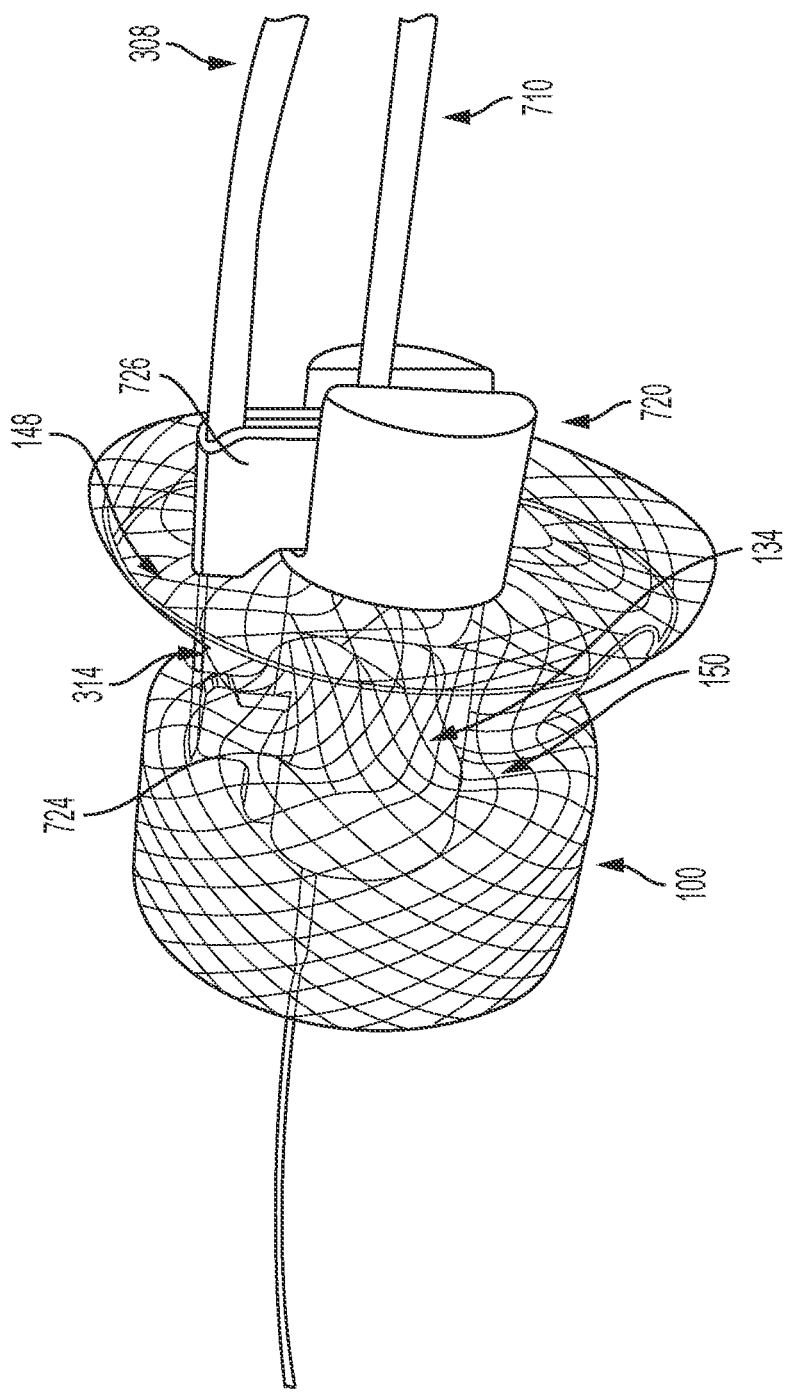

In the delivery configuration shown in FIG. 21A, the first and second extendable arms 724 and 726 are shown at a first longitudinal distance from one another (e.g., a first distance between the first and second extendable arms 724 and 726 along the longitudinal axis of the locator capsule 722). In the deployed configuration shown in FIG. 21C, the first and second extendable arms 724 and 726 are shown at a second longitudinal distance from one another (e.g., a second distance between the first and second extendable arms 724 and 726 along the longitudinal axis of the locator capsule 722). As shown, the second longitudinal distance is less than the first longitudinal distance. Providing a mechanism that allows the first and second extendable arms 724 and 726 to be drawn closer to one another provides that the first and second extendable arms 724 and 726 can engage the gastrointestinal device to help constrain a longitudinal position of the delivery system 700 relative to the gastrointestinal device as the suture tethers are delivered and deployed. For instance, as shown in FIGS. 23A and 23B, the first and second extendable arms 724 and 726 can engage the gastrointestinal device and pinch the proximal and distal wall flanges between the first and second extendable arms 724 and 726 to help constrain a longitudinal position of the delivery system 700 relative to the gastrointestinal device as the suture tethers are delivered and deployed, as shown and discussed further below.

In some examples, the second extendable arm 726 includes an aperture sized to accommodate the first elongate element 711 passing through the aperture and extending to the first extendable arm 724. For example, as shown in FIG. 22, the first elongate element 711 extends through an aperture in a portion of the body of the second extendable arm 726 and extends therefrom to the first extendable arm 724. It is to be appreciated that while the first elongate element 711 extends through a portion of the body of the second extendable arm 726, the first elongate element 711 is not coupled to the second extendable arm 726 in that the first elongate element 711 is operable to slide relative to the second extendable arm 726. Likewise, Thus, the second extendable arm 726 is operable to slide relative to the first elongate element 711.

In some examples, the locator system 720 further includes a biasing member 736. The biasing member 736 may include one or more resilient elements, such as one or more springs. In some examples, the biasing member 736 is configured to bias the first extendable arm 724 away from the second extendable arm 726 and/or bias the second extendable arm 726 away from the first extendable arm 724. In some examples, the biasing member 736 is alternatively configured to bias the first extendable arm 724 toward the second extendable arm 726 and/or bias the second extendable arm 726 toward the first extendable arm 724. The biasing member 736 may bias the first and/or second extendable arm 724 and 726 when the delivery system 700 is in the delivery configuration (e.g., the first and second extendable arms 724 and 726 are stowed within the locator capsule 722). Alternatively, the biasing member 736 may bias the first and/or second extendable arm 724 and 726 when delivery system 700 is in the deployed configuration (e.g., the first and second extendable arms 724 and 726 are extended radially outwardly from the locator capsule 722).

In some examples, the biasing member 736 is situated between the first and second extendable arms 724 and 726. For example, as shown in FIG. 22, the biasing member 736 extends between the first and second extendable arms 724 and 726. For the delivery system 700 shown in FIG. 22, the biasing member 736 is configured to bias the first and second extendable arms 724 and 726 away from one another when the delivery system is in the deployed configuration (e.g., the first and second extendable arms 724 and 726 are extended radially outwardly from the locator capsule 722). As shown, the first elongate element 711 extends through the biasing member 736 as it extends from the second extendable arm 726 to the first extendable arm 724.

Additionally, while the delivery system 700 is depicted in FIG. 22 with the elongate element 308 removed, it is to be understood that the elongate element 308 may be coupled with the second extendable arm 726. For instance, as shown in FIG. 22, the second extendable arm 726 includes a channel 738 that is configured to accommodate the elongate element 308 (e.g., as shown in FIGS. 21A-21D, and 23A-24B). In some examples, the channel 738 may be configured such that the elongate element 308 is removably coupleable with the locator system 720. In some other examples, the elongate element 308 is fixedly coupled with the locator system 720.

Consistent with the discussion above and the configuration of the locator capsule 722 shown in FIG. 22, as the relative distance between the first and second extendable arms 724 and 726 is decreased, the relationship between the protrusions 728 and 730 and the first and second channels 732 and 734 causes the first and second extendable arms 724 and 726 to extend radially outwardly from the locator capsule 722 as shown in FIGS. 21A-21C.

In some examples, by translating the first and second extendable arms 724 and 726 closer to one another as they are radially outwardly extended from the locator capsule 722, the first and second extendable arms 724 and 726 can actuate to hold the proximal and distal wall flanges of the gastrointestinal device to stabilize the delivery system 700 as the suture tethers 200 are delivered and deployed. For instance, once the first and second extendable arms 724 and 726 of the locator system 720 engage the gastrointestinal device, the needle 314 can be advanced from the elongate element 308 and reliably puncture the gastrointestinal device and the anatomy at a known and controlled location. In some examples, the delivery system 700 thus provides that the needle 314 and the suture tethers 200 are delivered and deployed at a designated radial distance relative to a central longitudinal axis of the gastrointestinal device.

Figure 24A:
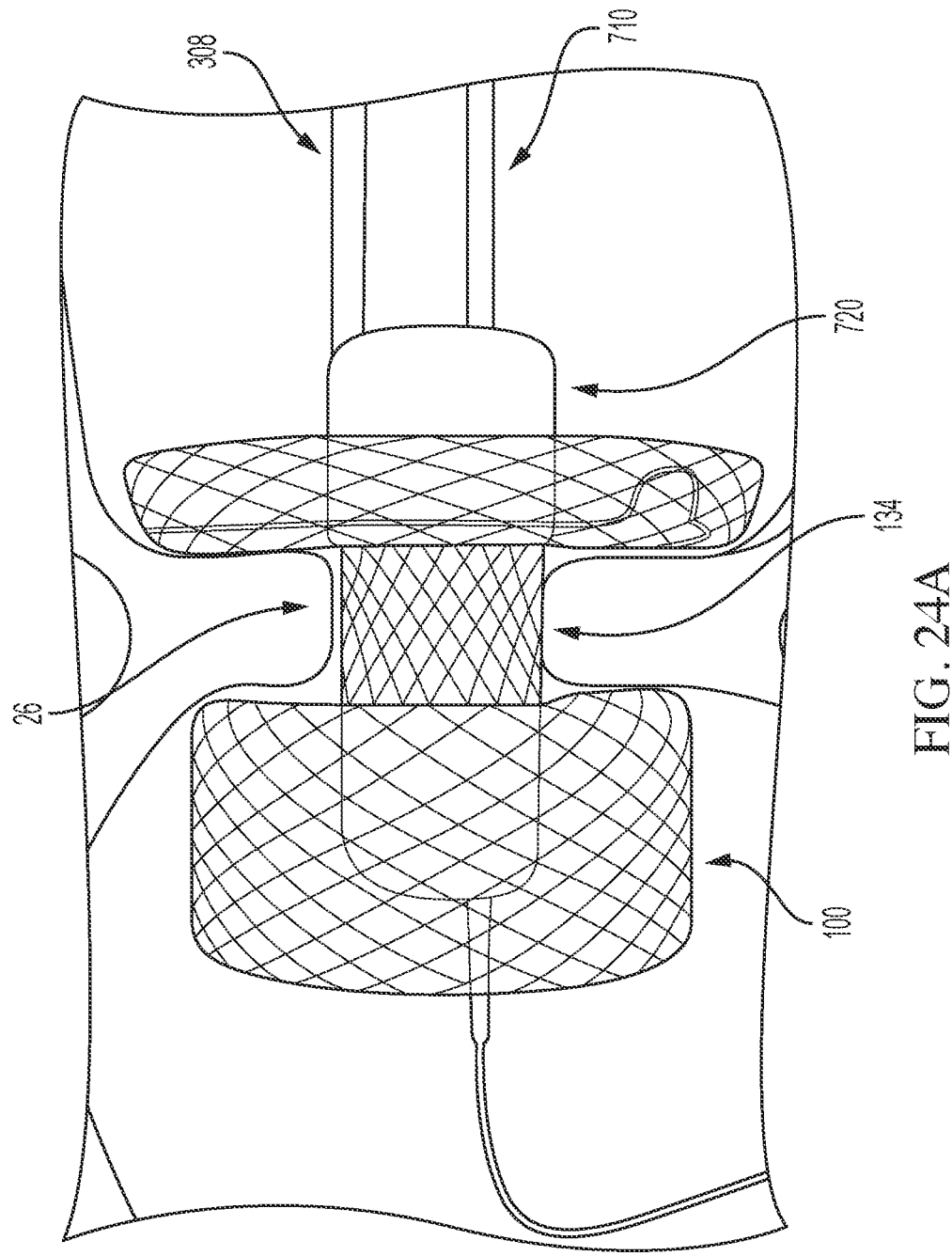
FIGS. 24A-24B is a cross-sectional view of a portion of the digestive tract in a human body with a gastrointestinal implant delivery system in combination with a gastrointestinal device, according to some embodiments
Figure 24B:
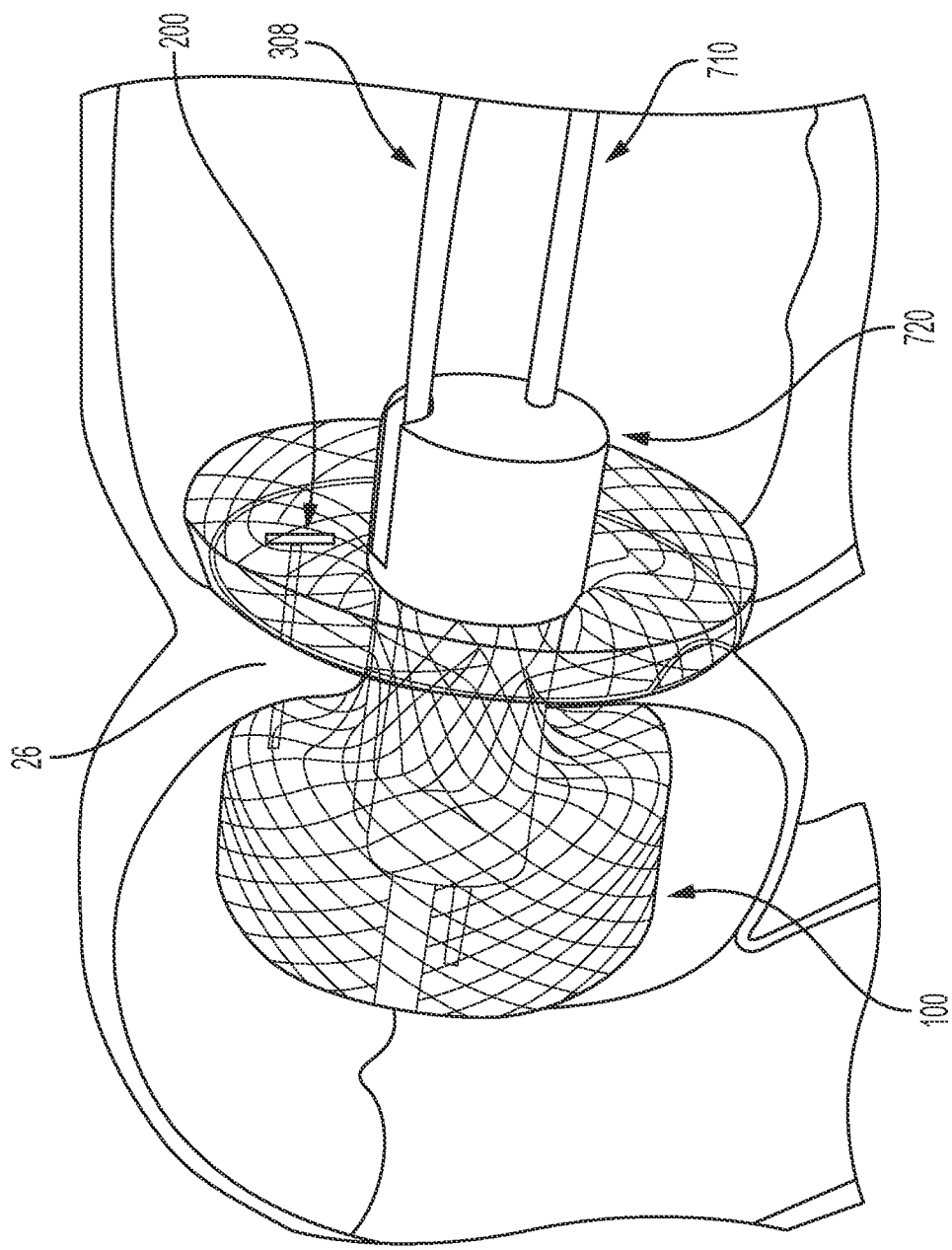

Turning now to FIGS. 23A-24B, operation of the delivery system 700 with a gastrointestinal device 100 is shown. FIGS. 23A-23B illustrate the delivery system 700 in combination with a gastrointestinal device 100 outside of a biological anatomy to clearly depict the interactions between the delivery system 700 and the gastrointestinal device 100. FIGS. 24A-24B illustrate the delivery system 700 in combination with a gastrointestinal device 100 within a patient's anatomy as the suture tether 200 is delivered and deployed.

As shown in FIG. 23A, the locator capsule 722 extends through the through-lumen of the gastrointestinal device 100, with the first and second extendable arms 724 and 726 radially outwardly extended such that the first extendable arm 724 engages the distal wall flange 150 of the gastrointestinal device 100, and such that the second extendable arm 726 engages the proximal wall flange 148. As shown in FIG. 23B, the needle 314 has been advanced from the elongate element 308 such that the needle extends between the first and second extendable arms 724 and 726 and such that the needle extends across the neck portion 134 of the gastrointestinal device 100 from the proximal wall flange 148 to the distal wall flange 150.

FIG. 24A shows the locator capsule 722 extends through the through-lumen of the gastrointestinal device 100 with the gastrointestinal device 100 deployed within the anatomy, and across the pyloric sphincter 26 in particular. FIG. 24B shows a suture tether 200 that has been delivered through the gastrointestinal device 100 and the pyloric sphincter 26 and deployed to help secure the gastrointestinal device 100 to the anatomy and to help minimize a potential of dislodgement of the gastrointestinal device 100 from the anatomy. As shown in FIG. 24B, after the suture tether 200 is delivered and deployed, the needle 314 is retractable to within the elongate element 308 and the first and second extendable arms 724 and 726 can be actuated such that they reside within the locator capsule 722 in the delivery configuration. With the delivery system 700 in the configuration shown in FIG. 24B, the delivery system can be rotated about a longitudinal axis of the gastrointestinal device 100 (e.g., from the 12 o'clock position to the four o'clock position) such that anther suture tether 200 can be delivered through the gastrointestinal device 100 and the anatomy and deployed to further help minimize a potential of dislodgement of the gastrointestinal device 100 from the anatomy. Alternatively, with the delivery system 700 in the configuration shown in FIG. 24B, the delivery system 700 can be withdrawn from the anatomy, where the locator system 720, the catheter 710 and the elongate element 308 are removed from the anatomy, and where the gastrointestinal device 100 and the suture tethers 200 remain within the anatomy.

It is to be appreciated that while the delivery system 700 is depicted with two extendable arms that straddle a neck portion of a gastrointestinal device, delivery systems like the delivery system 700 are envisioned that include the second extendable arm 726 (e.g., an extendable arm that is positionable proximal to a proximal wall flange of a gastrointestinal device) without requiring the first extendable arm (e.g., an extendable arm that is positionable proximal to a proximal wall flange of a gastrointestinal device). In some such examples, the delivery system could rely, in part, on friction between a locator capsule extending through the through-lumen of the gastrointestinal device for maintaining a longitudinal position of the delivery system while the suture tether 200 is delivered and deployed.

Figure 25:
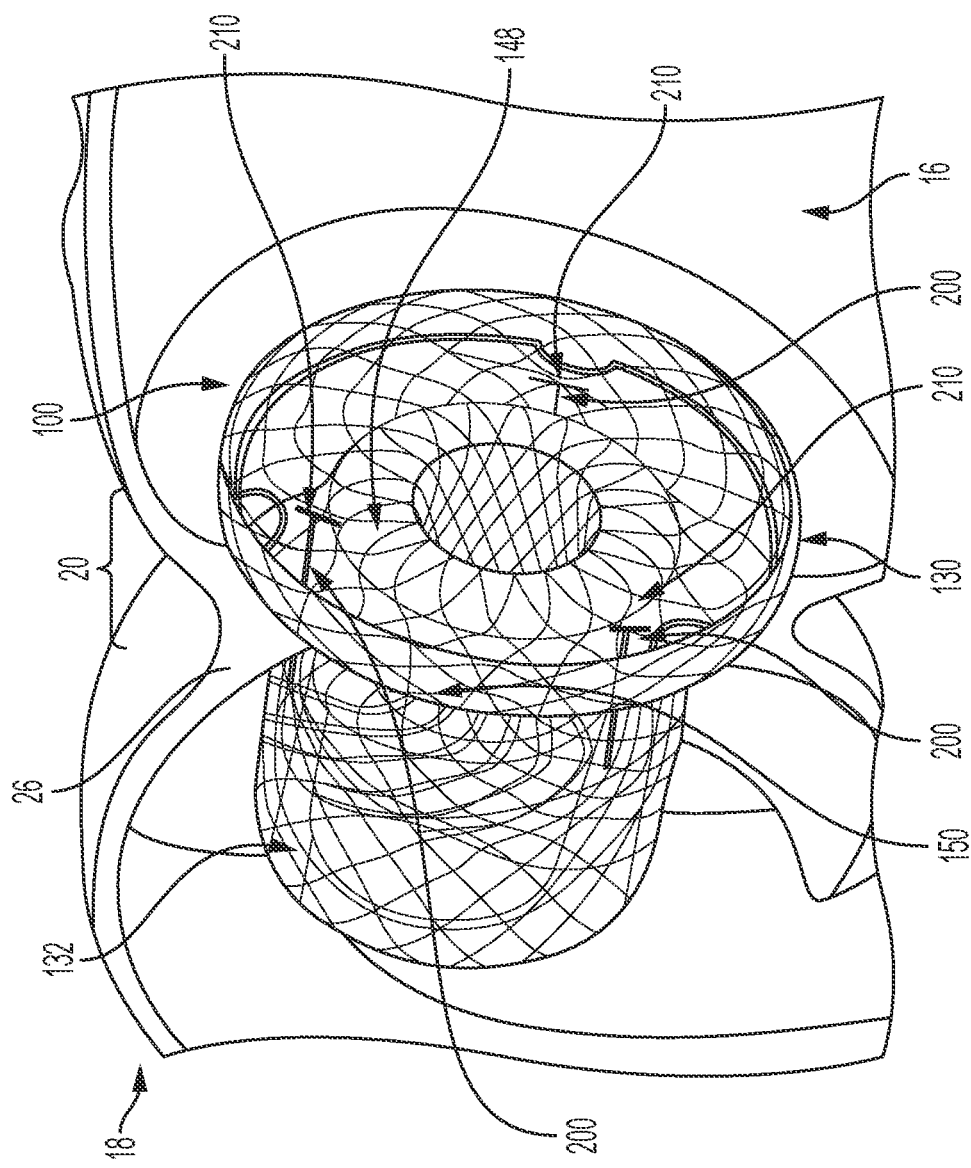
FIG. 25 is a cross-sectional view of a portion of the digestive tract in a human body with a gastrointestinal device positioned across the pylorus, according to some embodiments, according to some embodiments.

FIG. 25 shows the gastrointestinal device 100 delivered within the anatomy with a plurality of suture tethers 200. Specifically, as shown in FIG. 20, suture tethers 200 are situated in each of the twelve o'clock position, the four o'clock position, and the eight o'clock position. Each suture tether 200 extends through the proximal wall flange 148, through the pyloric sphincter 26, and through the distal wall flange 150 at the twelve o'clock position, such that associated first retaining tabs 210 are situated proximal to the proximal wall flange 148, and such that associated second retaining tabs 212 is situated distal to the distal wall flange 150.

Thus, it will be appreciated that using the methods described herein, a device, such as the gastrointestinal device 100 shown in FIG. 1 can be secured to the surrounding anatomy via a secondary anchoring mechanism so as to minimize a potential for dislodgment and migration. In various embodiments, using the methods described herein, the suture tethers 200 and the gastrointestinal device 100 can be removed from within the patient without using surgery, for example, without forming an incision into the body of the patient.

It should be appreciated that while the above discussed examples are illustrated and described with regard to a gastrointestinal device used in association with the pylorus, the devices, systems, and methods discussed herein may be utilized in other anatomical areas without departing from the spirit or scope of the present disclosure. Thus, the examples illustrated and described above should not be interpreted as limiting.

Numerous characteristics and advantages have been set forth in the preceding description, including various alternatives together with details of the structure and function of the devices and/or methods. Moreover, the inventive scope of the various concepts addressed in this disclosure has been described both generically and with regard to specific examples. The disclosure is intended as illustrative only and as such is not intended to be exhaustive. For example, the various embodiments of the present disclosure are described in the context of medical applications but can also be useful in non-medical applications. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A gastrointestinal implant system comprising:
an implant configured to be implanted within a pylorus of a patient, the implant formed of a braided wire structure having a proximal portion including a proximal wall flange, a distal portion including a distal wall flange, and a neck portion situated between the proximal and distal portions, the neck portion being configured to span a pyloric sphincter of the pylorus when implanted, and wherein the proximal wall flange and the distal wall flange are each defined by a necked portion such that the proximal wall flange and the distal wall flange are configured to be spaced from a pyloric sphincter at the necked portion when implanted in a patient;
an anti-migration anchor including an elongate element having a length greater than a distance between the proximal wall flange and the distal wall flange, a first retention feature coupled to the elongate element, and a second retention feature coupled to the elongate element, the anti-migration anchor configured such that the elongate element is operable to be inserted partially through the braided wire structure of each of the proximal portion and the distal portion of the implant to span the neck portion of the implant such that the first retention feature is positionable proximal to and in contact with the proximal portion of the implant and such that the second retention feature is positionable distal to and in contact with the distal portion of the implant.

2. The system of claim 1, wherein the first and second retention features are configured to transition between delivery and deployed configurations.

3. The system of claim 2, wherein in the delivery configuration, the first and second retention features extend along the elongate element, and wherein in the deployed configuration, the first and second retention features extend transverse to the elongate element.

4. The system of claim 2, wherein the first retention feature includes a first end, a second end, and a middle portion situated between the first and second ends, and wherein the elongate element is coupled to the middle portion.

5. The system of claim 2, wherein one or more of the first and second retention features are biased to transition to the deployed configuration when not constrained.

6. The system of claim 1, wherein the anti-migration anchor is configured to extend through a tissue situated between the proximal and distal portions of the implant, thereby securing the implant to the tissue, and wherein the proximal and distal portions and the neck of the implant form a primary anchor for anchoring the implant to the tissue, and wherein the anti-migration anchor forms a secondary anchor for anchoring the implant to the tissue.

7. The system of claim 1, wherein the anti-migration anchor operates to help maintain a geometry of the implant, and wherein the anti-migration anchor operates to provide at least one of: to minimize an amount of relative angulation between the proximal and distal portions of the implant by constraining a length between the proximal and distal portions of the implant, and to constrain an amount of deformation of one or more of the proximal and distal portions of the implant.

8. The system of claim 1, wherein the first and second retention features of the anti-migration anchor are configured such that they can only contact the proximal and distal portions of the implant and cannot come in direct contact with the pyloric tissue.

9. The system of claim 1, wherein the anti-migration anchor is configured to tether the implant to the pylorus when implanted.

10. The system of claim 1, wherein the anti-migration anchor is one or more of implantable after the implant is implanted and removable from the implant.

11. A method of securing a gastrointestinal implant within a pylorus of a patient, the method comprising:
    providing the implant formed of a braided wire structure having a proximal portion including a proximal wall flange, a distal portion including a distal wall flange, and a neck portion situated between the proximal and distal portions,
    deploying the implant within the pylorus such that the neck portion spans the pylorus with the proximal portion of the implant situated proximal to the pylorus and the distal portion situated distal to the pylorus;
    providing an anti-migration anchor including an elongate element having a length greater than a distance between the proximal wall flange and the distal wall flange, a first retention feature coupled to the elongate element, and a second retention feature coupled to the elongate element, and wherein the proximal wall flange and the distal wall flange are each defined by a necked portion such that the proximal wall flange and the distal wall flange are spaced from tissue of the pyloric sphincter at the necked portion;
    after deploying the implant, deploying the anti-migration anchor by inserting the anti-migration anchor into the braided wire structure of the proximal portion and the distal portion of the implant such that the anti-migration anchor spans the neck portion of the implant and punctures the proximal and distal portions of the implant, and such that the first retention feature is situated proximal to the proximal portion of the implant and such that the second retention feature is situated distal to the distal portion of the implant.

12. The method of claim 11, further comprising deploying the implant within the pylorus such that a tissue of the pylorus is situated proximate the neck portion and between the proximal and distal portions of the implant.

13. The method of claim 11, further comprising deploying the anti-migration anchor such that the anti-migration anchor punctures the tissue of the pylorus but does not penetrate the wall of the stomach or the small intestine in to the surrounding abdominal cavity.

14. The method of claim 11, further comprising deploying a plurality of anti-migration anchors such that each anti-migration anchor punctures the tissue.

* * * * *